(12) United States Patent
Maciag et al.

(10) Patent No.: US 9,168,266 B2
(45) Date of Patent: Oct. 27, 2015

(54) HYBRID DIAZENIUMDIOLATED COMPOUNDS, PHARMACEUTICAL COMPOSITIONS, AND METHOD OF TREATING CANCER

(71) Applicant: The United States of America, as represented by the Secretary, Department of Health and Human Services, Washington, DC (US)

(72) Inventors: Anna E. Maciag, Frederick, MD (US); Larry K. Keefer, Bethesda, MD (US); Joseph E. Saavedra, Thurmont, MD (US); Xinhua Ji, Frederick, MD (US); Vandana Kumari, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/352,096

(22) PCT Filed: Oct. 18, 2012

(86) PCT No.: PCT/US2012/060785
§ 371 (c)(1),
(2) Date: Apr. 16, 2014

(87) PCT Pub. No.: WO2013/059433
PCT Pub. Date: Apr. 25, 2013

(65) Prior Publication Data
US 2014/0315865 A1 Oct. 23, 2014

Related U.S. Application Data

(60) Provisional application No. 61/549,862, filed on Oct. 21, 2011.

(51) Int. Cl.
| | | |
|---|---|---|
| C07D 403/10 | (2006.01) | |
| A61K 31/655 | (2006.01) | |
| A61K 45/06 | (2006.01) | |
| A61K 31/69 | (2006.01) | |
| A61K 31/704 | (2006.01) | |
| C07D 237/30 | (2006.01) | |
| C07D 295/28 | (2006.01) | |
| C07C 291/02 | (2006.01) | |
| C07D 237/32 | (2006.01) | |

(52) U.S. Cl.
CPC .............. *A61K 31/655* (2013.01); *A61K 31/69* (2013.01); *A61K 31/704* (2013.01); *A61K 45/06* (2013.01); *C07C 291/02* (2013.01); *C07D 237/30* (2013.01); *C07D 237/32* (2013.01); *C07D 295/28* (2013.01); *C07D 403/10* (2013.01)

(58) Field of Classification Search
CPC ... C07D 241/04; C07D 403/10; A61K 31/655
See application file for complete search history.

(56) References Cited

U.S. PATENT DOCUMENTS
2001/0025052 A1    9/2001   Hrabie et al.

FOREIGN PATENT DOCUMENTS
| CA | 2780633 A1 | 5/2011 |
|---|---|---|
| WO | WO 2011/060215 A1 | 5/2011 |

OTHER PUBLICATIONS

Chakrapani et al., "Synthesis and in vitro anti-leukemic activity of structural analogues of JS-K, an anti-cancer lead compound," *Bioorg. & Med. Chem. Lett.*, (2008) 950-953, 18.
Chakrapani et al., "Synthesis, mechanistic studies, and anti-proliferative activity of glutathione/glutathione S-transferase-activated nitric oxide prodrugs," *Bioorg. & Med. Chem.*, (Sep. 30, 2008) 9764-9771, 16.
International Preliminary Report on Patentability, Application No. PCT/US2012/060785, dated Apr. 22, 2014.
International Search Report, Application No. PCT/US2012/060785, dated Jul. 1, 2013.

(Continued)

*Primary Examiner* — Robert Havlin
(74) *Attorney, Agent, or Firm* — Leydig, Voit & Mayer

(57) ABSTRACT

Disclosed are hybrid compounds that release both nitric oxide and a moiety that inhibits poly (ADP-ribose) polymerase (PARP), e.g., a compound or a pharmaceutically acceptable salt thereof of formula (I), wherein $R^{1-4}$ and m-p are as described herein. Also disclosed are pharmaceutical compositions and methods of use including treating cancer and enhancing the chemotherapeutic treatment of chemotherapeutic agents and high energy radiation.

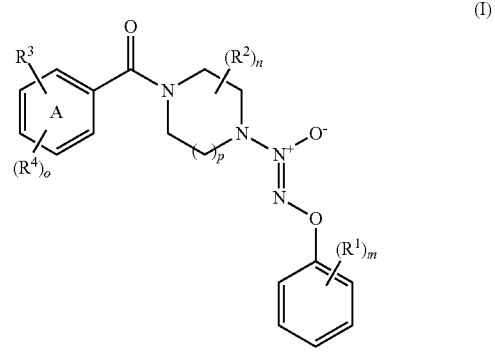

23 Claims, 8 Drawing Sheets

(56) References Cited

OTHER PUBLICATIONS

Kiziltepe et al., "JS-K, a GST-activated nitric oxide generator, induces DNA double-strand breaks, activates DNA damage response pathways, and induces apoptosis in vitro and in vivo in human multiple myeloma cells," *Blood*, (2007) 709-718, 110, 2.

Maciag et al., "The Nitric Oxide Prodrug JS-K Is Effective against Non-small-Cell Lung Cancer Cells *in vitro* and *in vivo*: Involvement of Reactive Oxygen Species," *The Journal of Pharmacology and Experimental Therapeutics*, (Oct. 20, 2010) 313-320, 336, 2.

Maciag et al., "Nitric Oxide (NO) Releasing Poly ADP-ribose Polymerase 1 (PARP-1) Inhibitors Targeted to Glutathione S-Transferase P1-Overexpressing Cancer Cells," *J. Med. Chem.*, (2014) 2292-2302, 57.

Menear et al., "Novel alkoxybenzamide inhibitors of poly(ADP-ribose) polymerase," *Bioorg. Med. Chem. Lett.*, (2008) 3942-3945, 18.

Menear et al., "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1," *J. Med. Chem.*, (2008) 6581-6591, 51.

Nandurdikar et al., "Synthesis and evaluation of piperazine and homopiperazine analogues of JS-K, an anti-cancer lead compound," *Bioorg. & Med. Chem. Lett.*, (2009) 2760-2762, 19.

Shami et al., "JS-K, a Glutathione/Glutathione S-Transferase-activated Nitric Oxide Donor of the Diazeniumdiolate Class with Potent Antineoplastic Activity," *Mol. Cancer Ther.*, (2003) 409-417, 2.

Shami et al., "Antitumor Activity of JS-K [$O^2$-(2,4-Dinitrophenyl) 1-[(4-Ethoxycarbonyl)piperazin-1-yl]diazen-1-ium-1,2-diolate] and Related $O^2$-Aryl Diazeniumdiolates in Vitro and in Vivo," *J. Med. Chem.*, (2006) 4356-4366, 49.

Written Opinion of the International Searching Authority, Application No. PCT/US2012/060785, dated Jul. 1, 2013.

HYBRID DIAZENIUMDIOLATED COMPOUNDS, PHARMACEUTICAL COMPOSITIONS, AND METHOD OF TREATING CANCER

CROSS-REFERENCE TO RELATED APPLICATIONS

This patent application is a U.S. National Phase of International Patent Application No. PCT/US2012/060785, filed Oct. 18, 2012, which claims the benefit of U.S. Provisional patent Application No. 61/549,862, filed Oct. 21, 2011, each of which is incorporated by reference.

BACKGROUND OF THE INVENTION

Poly(ADP-ribose) polymerase (PARP) is an attractive antitumor target because of its vital role in DNA repair. Many anti-cancer therapies, including alkylating agents and radiation, produce DNA strand breaks and PARP is an essential player in the repair of this type of DNA damage. PARP inhibitors have emerged as a promising therapeutic class of compounds, and numerous PARP inhibitors have advanced into clinical trials.

The homologous recombination (HR) DNA repair pathway is critical for the repair of DNA double-strand breaks. HR deficiency leads to a dependency on error-prone DNA repair mechanisms, with consequent genomic instability and oncogenesis. Tumor-specific HR defects may be exploited through a synthetic lethal approach for the application of anticancer therapeutics, including PARP inhibitors. The demonstration of single-agent antitumor activity of PARP inhibitors in cancers with deficiencies in breast cancer susceptibility BRCA1 and BRCA2 provides strong evidence for the clinical application of this approach. Mutations in the BRCA1/2 genes are associated with HR-mediated double strand break repair defects, and inhibition of the base-excision repair-mediated single strand break repair via PARP inhibition results in synthetic lethality. For example, olaparib (AZD-2281/KU-0059436, Astra Zeneca) is a phthalazinone PARP inhibitor that is in phase II clinical trials as an oral single agent for the treatment of BRCA-deficient breast and ovarian cancers (Vasiliou at al., *Drugs Future,* 34: 101-105 (2009)).

Nitric oxide (NO) is a signaling molecule, a toxicant, and an antioxidant under various conditions, with a broad spectrum of actions in physiological and pathological processes. Diazeniumdiolate-based nitric oxide-releasing prodrugs are a growing class of promising NO-based cancer therapeutics. $O^2$-(2,4-Dinitrophenyl)-1-[(4-ethoxycarbonyl)piperazin-1-yl]diazen-1-ium-1,2-diolate (JS-K) has proven effective against leukemia, multiple myeloma, prostate, liver, and non-small cell lung cancer (NSCLC) cancer cell lines in vitro and in vivo (see, e.g., Shami et al., *Mol. Cancer Ther.,* 2: 409-417 (2003); Shami et al., *J. Med. Chem.,* 49: 4356-4366 (2006); Kiziltepe et al., *Blood,* 110: 709-718 (2007); and Maciag et al., *J. Pharmacol. Exp. Ther.,* 336: 313-320 (2011)).

Thus, even though current therapies exist, there is an unmet need for agents suitable for treating cancers, particularly agents that can both damage DNA and inhibit DNA repair in cancer cells.

BRIEF SUMMARY OF THE INVENTION

The invention provides novel hybrid compounds which act as dual prodrugs comprising a functional portion of a PARP inhibitor and a diazeniumdiolate moiety $N_2O_2^-$. Accordingly, the compounds of the invention release both a PARP-inhibiting moiety and nitric oxide under physiological conditions.

The invention provides a hybrid diazeniumdiolated compound of formula (I)

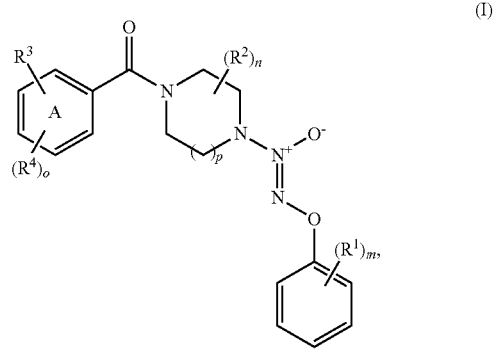

in which $R^1$ is H or a moiety independently selected from $N_3$, CN, $NO_2$, CHO, NCS, SCN, F, Cl, Br, I, $OCF_3$, O—N=N(O)$NR'_2$, $SO_3H$, $B(OH)_2$, $PO(OH)_2$, $PO(OH)(OR')$, $PO(OR')_2$, $SO_2NHOH$, $SO_2NH_2$, $CONH_2$, CONHOH, SR', SOR', $SO_2R'$, $SO_2NHR'$, $SO_2N(R')R'$, $SO_2NHCON(R')R'$, COOR', COR', CONHR', $CON(R')R'$, $CONHSO_2N(R')R'$, NHCOR', N(R')COR', $NHSO_2R'$, $N(R')SO_2R'$, $NH_2R'^+M^-$, $NHR'_2^+M^-$, and $NR'_3^+M^-$, wherein each R' is the same or different and is selected from H, $C_1$-$C_6$ alkyl, and $CY_3$, wherein Y is F, Cl, or Br; $M^-$ is a counterion; wherein the $C_1$-$C_6$ alkyl is optionally substituted with one or more substituents selected from halo, OH, alkoxy, CN, amino, and $NO_2$;

$R^2$ is independently selected from H, CN, formyl, carboxy, amido, and a moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, and alkoxycarbonyloxy, and wherein each moiety is optionally further substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

$R^3$ comprises a moiety selected from aryl, heteroaryl, and heterocycloalkyl, each of which is optionally substituted with at least one substituent selected from $NHR^5CO$, $OR^6$, carboxy, carboxyalkyl, amido, alkyl, $NO_2$, halo, mercapto, thioalkoxy, cyano, alkoxy, $C_{2-7}$ haloalkyl, heterocycloalkyl, and aryl, wherein $R^5$ and $R^6$ are each individually selected from H, acyl, and $C_{1-6}$ alkyl, and a linker, wherein the moiety is attached to phenyl ring A through the linker;

$R^4$ is independently selected from H, halo, OH, CN, $NO_2$, sulfonato, formyl, carboxy, mercapto, amido, amino, or a moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, and wherein each moiety is optionally further substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

m is independently 0 to 5; n and o are independently 0 to 4; and p is 1 or 2;

or a pharmaceutically acceptable salt thereof.

The invention further provides a hybrid diazeniumdiolated compound of formula (II)

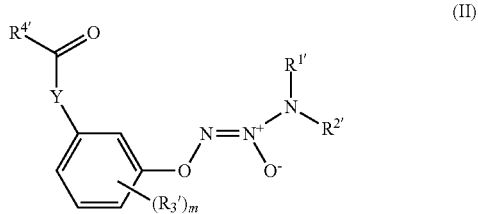

(II)

wherein $R^{1'}$ and $R^{2'}$ are each independently selected from alkyl, alkyl substituted with alkoxy, acyloxy, OH, halo, or benzyl, alkenyl, and alkenyl substituted with alkoxy, acyloxy, OH, halo, or benzyl, or $R^{1'}$ and $R^{2'}$, together with the nitrogen atom to which they are bonded, form a heterocyclyl, e.g., heterocycloalkyl, having at least one or more heteroatoms selected from O, S and N;

$R^{3'}$ is independently selected from H, CN, $NO_2$, sulfonato, formyl, carboxy, mercapto, amido, amino, alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, wherein each of said alkyl, aryl alkyl, aryl, heterocycloalkyl, heteroaryl, heteroaryl alkyl, hydroxyalkyl, haloalkyl, aminoalkyl, alkoxy, aryloxy, alkylamino, and dialkylamino is optionally substituted with one or more substituents selected from alkyl, alkenyl, alkynyl, aryl alkyl, aryl, heterocycloalkyl, heteroaryl, heteroaryl alkyl, OH, hydroxyalkyl, halo, haloalkyl, aminoalkyl, alkoxy, aryloxy, thioalkoxy, acyl, acyloxy, alkoxycarbonyl, alkoxycarbonyloxy, alkylamino, and dialkylamino;

m is independently 0 to 4;

Y is a linker selected from —$NR^{9'}$—,

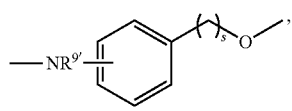

—S—, and —O—, wherein $R^{9'}$ is selected from H and $C_1$-$C_6$ alkyl, and s is 0 to 4;

$R^{4'}$ is a moiety selected from

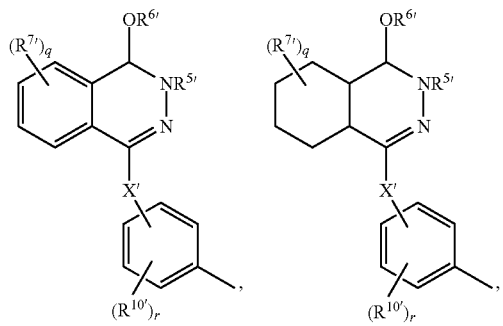

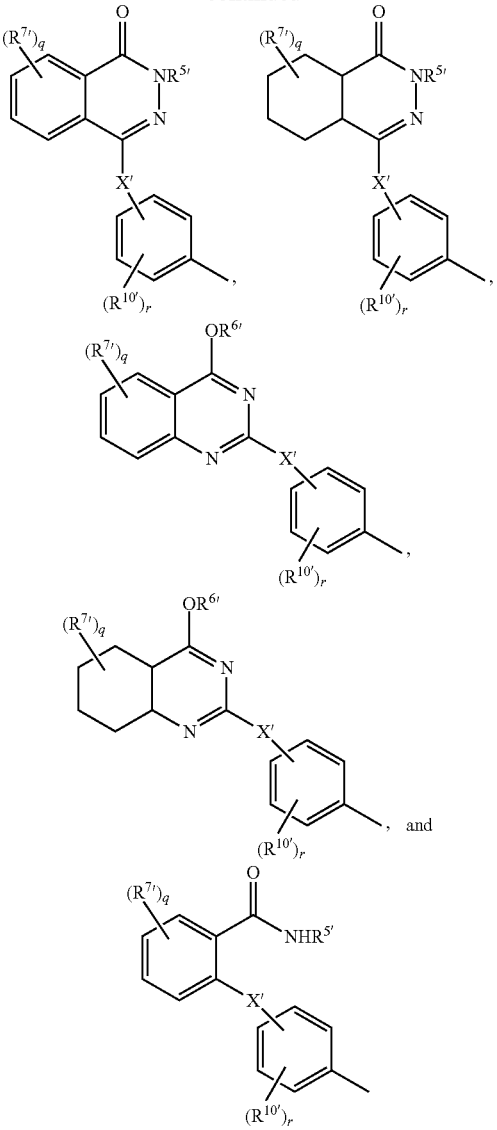

wherein $R^{5'}$ and $R^{6'}$ are each independently selected from H, acyl, and $C_{1-6}$ alkyl;

$R^{7'}$ is each independently selected from H, halo, $NO_2$, CN, OH, alkoxy, mercapto, thioalkoxy, amino, $C_{1-6}$ alkyl, $C_{2-7}$ haloalkyl, heterocycloalkyl, and aryl;

$R^{10'}$ is each independently selected from H, halo, OH, CN, $NO_2$, sulfonato, formyl, carboxy, mercapto, amido, amino, or an optionally substituted moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

X' is a linker selected from —$(CH_2)_r$—, —O—, —C(O)—, —O$(CH_2)_r$—, —$(CH_2)_r$O—, —S—, —S$(CH_2)_r$—, —$(CH_2)_r$S—, —$NR^{8'}$—, —$(CH_2)_rNR^{8'}$—, —$NR^{8'}(CH_2)_r$—, —$NR^{8'}C(O)NR^{8'}$—, and —$C(O)NR^{8'}C(O)$—; wherein r is 1 to 5; and $R^{8'}$ is selected from H and $C_1$-$C_6$ alkyl; and q and r are independently 0 to 4;

or a pharmaceutically acceptable salt thereof.

The invention also provides pharmaceutical compositions and methods of treating cancer by the use of the above compounds. For example, in one aspect, the method is applicable to treating cancers wherein the cancer cell has an elevated ROS content and/or decreased levels of OGG1. The invention further provides a method for enhancing the chemotherapeutic treatment of cancer and/or radiation treatment of cancer.

BRIEF DESCRIPTION OF THE SEVERAL VIEWS OF THE DRAWING(S)

DETAILED DESCRIPTION OF THE INVENTION

Figure 1:
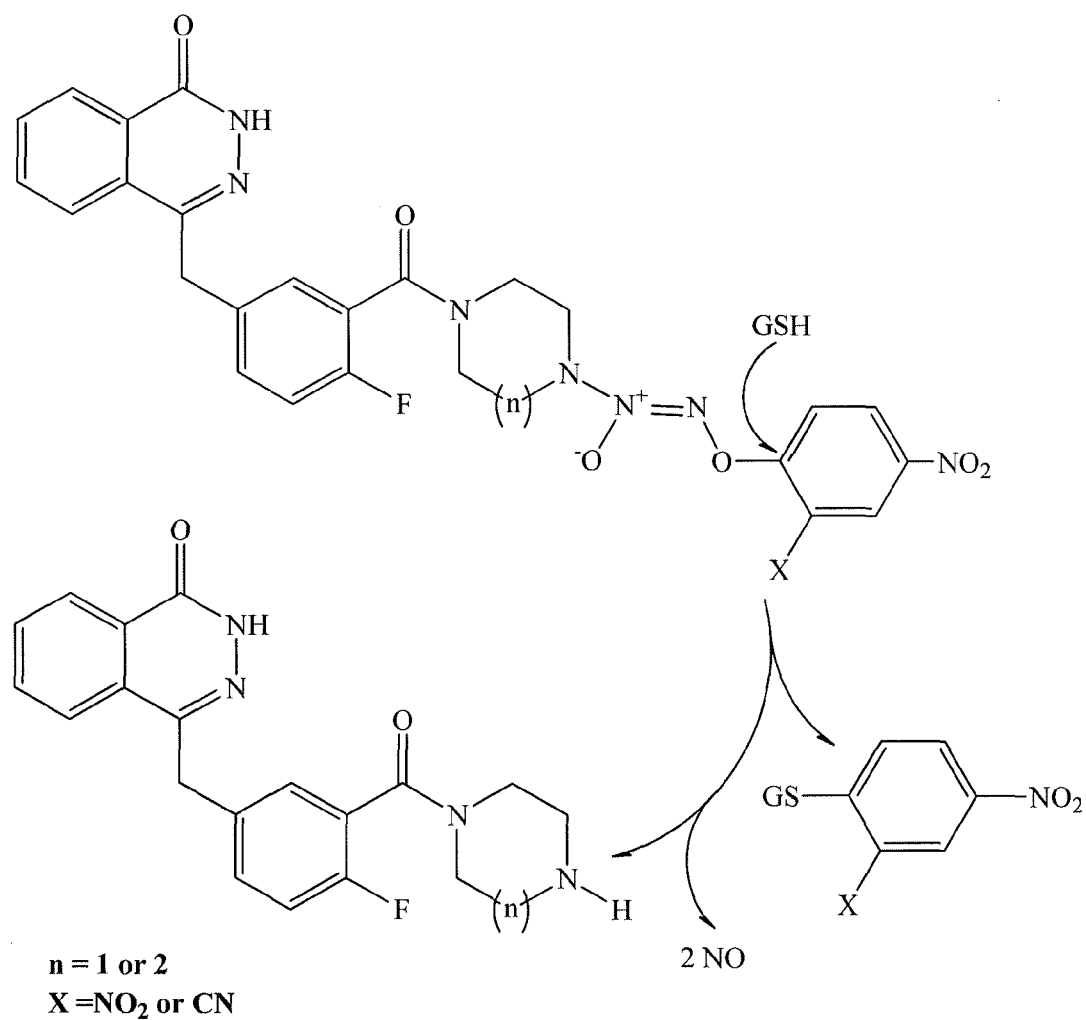
FIG. 1 depicts a schematic illustrating a compound of formula (I) and a proposed mechanism of its decomposition in the presence of glutathione (GSH).

It is envisioned that the hybrid compounds of the invention can deliver DNA-damaging NO and a PARP inhibitor simultaneously to a cancer cell. FIG. 1 illustrates an example of a prodrug of the invention and a proposed mechanism of NO/PARP inhibitor release. It is believed that the inventive prodrugs are activated by glutathione/glutathione S-transferase P1 (GSH/GSTP1), a phase II detoxifying enzyme that is frequently overexpressed in cancer cells, and release cytotoxic NO and a PARP inhibitor in the target cancer cell. Preferably the target cell is a cancer cell that is high in GSH/GSTP1. Therefore, the compounds of the present invention allow a concurrent release of cytotoxic components upon metabolic activation in the cancer cell, which should have advantages over delivering two independent conventional therapeutic molecules.

In accordance with an embodiment, the invention provides a hybrid compound of formula (I)

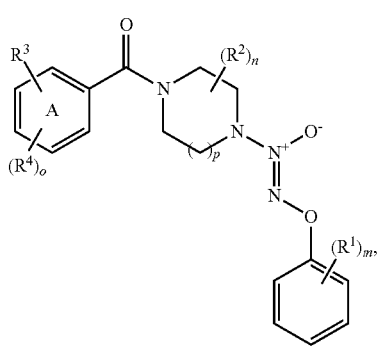

(I)

wherein $R^1$ is H or a moiety independently selected from $N_3$, CN, $NO_2$, CHO, NCS, SCN, F, Cl, Br, I, $OCF_3$, O—N=N(O)NR'$_2$, $SO_3H$, $B(OH)_2$, $PO(OH)_2$, PO(OH)(OR'), $PO(OR')_2$, $SO_2NHOH$, $SO_2NH_2$, $CONH_2$, CONHOH, SR', SOR', $SO_2R'$, $SO_2NHR'$, $SO_2N(R')R'$, $SO_2NHCON(R')R'$, COOR', COR', CONHR', CON(R')R', $CONHSO_2N(R')R'$, NHCOR', N(R')COR', $NHSO_2R'$, $N(R')SO_2R'$, $NH_2R'^+M^-$, $NHR'_2{}^+M^-$, and $NR'_3{}^+M^-$, wherein each R' is the same or different and is selected from H, $C_1$-$C_6$ alkyl, and $CY_3$, wherein Y is F, Cl, or Br; $M^-$ is a counterion; wherein the $C_1$-$C_6$ alkyl is optionally substituted with one or more substituents selected from halo, OH, alkoxy, CN, amino, and $NO_2$;

$R^2$ is independently selected from H, CN, formyl, carboxy, amido, and a moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, and alkoxycarbonyloxy, and wherein each moiety is optionally further substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

$R^3$ comprises a moiety selected from aryl, heteroaryl, and heterocycloalkyl, each of which is optionally substituted with at least one substituent selected from $NHR^5CO$, $OR^6$, carboxy, carboxyalkyl, amido, alkyl, $NO_2$, halo, mercapto, thioalkoxy, cyano, alkoxy, $C_{2-7}$ haloalkyl, heterocycloalkyl, and aryl, wherein $R^5$ and $R^6$ are each individually selected from H, acyl, and $C_{1-6}$ alkyl, and a linker, wherein the moiety is attached to phenyl ring A through the linker;

$R^4$ is independently selected from H, halo, OH, CN, $NO_2$, sulfonato, formyl, carboxy, mercapto, amido, amino, or a moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, and wherein each moiety is optionally further substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

m is independently 0 to 5; n and o are independently 0 to 4; and p is 1 or 2;

or a pharmaceutically acceptable salt thereof.

In certain embodiments, $R^1$ is H or a moiety independently selected from $N_3$, CN, $NO_2$, CHO, NCS, SCN, F, Cl, Br, I, $OCF_3$, $SO_3H$, $B(OH)_2$, $PO(OH)_2$, PO(OH)(OR'), $PO(OR')_2$, $SO_2NHOH$, $SO_2NH_2$, $CONH_2$, CONHOH, SR', SOR', $SO_2R'$, $SO_2NHR'$, $SO_2N(R')R'$, $SO_2NHCON(R')R'$, COOR', COR', CONHR', CON(R)R', $CONHSO_2N(R')R'$, NHCOR', N(R')COR', $NHSO_2R'$, $N(R)SO_2R'$, $NH_2R'^+M^-$, $NHR'_2{}^+M^-$, and $NR'_3{}^+M^-$, wherein each R' is the same or different and is selected from H, $C_1$-$C_6$ alkyl, and $CY_3$, wherein Y is F, Cl, or Br; $M^-$ is a counterion (e.g., hydride, fluoride, bromide, iodide, nitride, phosphate, hydrogen phosphate, dihydrogen phosphate, sulfate, hydrogen suldate, nitrate, nitrite, chlorate, chlorite, hypochlorite, hypobromite, carbonate, hydrogen carbonate, acetate, formate, hydroxide, cyanide, and thiocyanate); wherein the $C_1$-$C_6$ alkyl is optionally substituted with one or more substituents selected from halo, OH, alkoxy, CN, amino, and $NO_2$. In other embodiments, $R^1$ is selected from H, CN, NO₂, NCS, SCN, F, Cl, Br, I, and OCF₃. Preferably, $R^1$ is CN or NO₂. More preferably, $R^1$ is NO₂.

In any of the foregoing embodiments or other embodiments, $R^2$ is H, CN, NO₂, carboxy, or an optionally substituted moiety selected from alkyl, aryl alkyl, aryl, heterocycloalkyl, heteroaryl, heteroaryl alkyl, hydroxyalkyl, haloalkyl, aminoalkyl, alkoxy, aryloxy, alkylamino, and dialkylamino. Preferably, $R^2$ is H or an optionally substituted alkyl. More preferably, $R^2$ is H.

In any of the foregoing embodiments or other embodiments, $R^3$ comprises a moiety selected from aryl and heteroaryl, each of which is optionally substituted with at least one substituent selected from NHR⁵CO, OR⁶, alkyl, NO₂, halo, CN, alkoxy, and $C_{1-7}$ haloalkyl, wherein $R^5$ and $R^6$ are each individually selected from H, acetyl, and $C_{1-6}$ alkyl, and a linker, wherein the moiety is attached to the phenyl ring through the linker. In an aspect, the linker of $R^3$ is selected from —(CH₂)ᵣ—, —O—, —C(O)—, —O(CH₂)ᵣ—, —(CH₂)ᵣO—, —S—, —S(CH₂)ᵣ—, —(CH₂)ₛS—, —NR⁸—, —(CH₂)ᵣNR⁸—, NR⁸(CH₂)ᵣ—, —NR⁸C(O)NR⁸—, and —C(O)NR⁸C(O)—; wherein r is 1 to 5; and $R^8$ is selected from H and $C_1$-$C_6$ alkyl. Preferably, $R^3$ is a moiety selected from

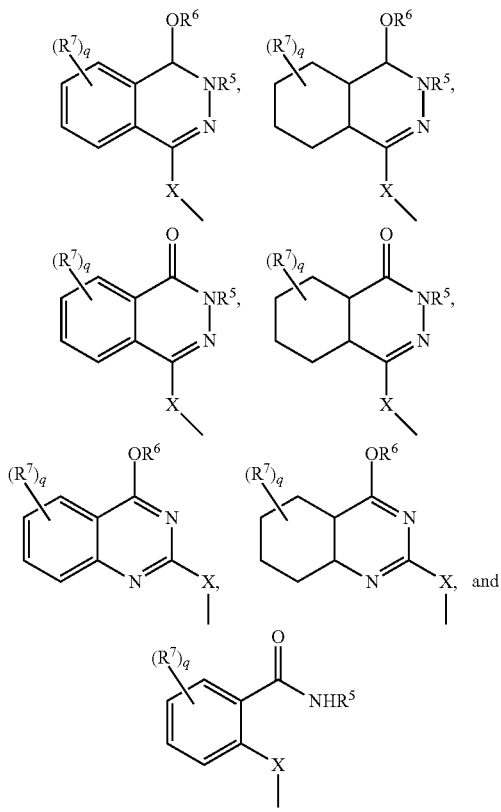

wherein
$R^5$ and $R^6$ are each individually selected from H, acetyl, and $C_{1-6}$ alkyl;
$R^7$ is selected from H, halo, NO₂, CN, OH, alkoxy, mercapto, thioalkoxy, amino, $C_{1-6}$ alkyl, $C_{1-7}$ haloalkyl, heterocycloalkyl, and aryl;
X is a linker selected from —CH₂—, —CH₂CH₂—, —O—, —OCH₂—, —CH₂O—, —NR⁸—, —CH₂NR⁸—, and —NR⁸CH₂—; wherein $R^8$ is selected from H and $C_1$-$C_6$ alkyl; and
q is 0 to 4.

In a preferred embodiment, $R^3$ is

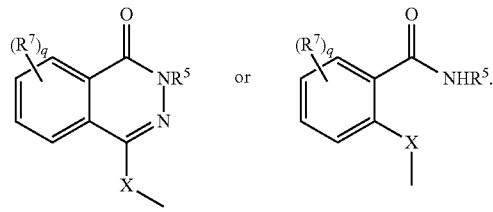

Particularly preferred are compounds in which $R^3$ is

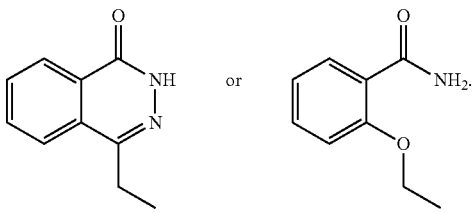

In any of the foregoing embodiments or other embodiments, $R^3$ can be present in formula (I) at any suitable position on the phenyl ring (e.g., the 1-, 2-, 3-, 4- or 5-position). Similarly, the substituent(s) $R^4$ are attached to the phenyl ring at any suitable position (e.g., the 1-, 2-, 3-, 4- or 5-position). In certain embodiments, $R^3$ is present in formula (I) at the 5-position on the phenyl ring. Additionally, $R^4$ preferably is attached to the phenyl ring at 2- and/or 4-positions.

In any of the foregoing embodiments or other embodiments, $R^7$ is H, OH, halo, or $C_{1-6}$ alkyl. Preferably, $R^7$ is H or halo.

In any of the foregoing embodiments or other embodiments, $R^4$ is H, OH, halo, or $C_{1-6}$ alkyl. Preferably, $R^4$ is H or halo.

In any of the embodiments, m is independently 0 to 4. In certain embodiments, m is 1, 2, 3, or 4.

In any of the foregoing embodiments, m preferably is 1 or 2 and/or n preferably is 0 or 1 and/or p preferably is 1 and/or o preferably is 0, 1, or 2.

In accordance with another embodiment, the invention provides a hybrid compound of formula (II)

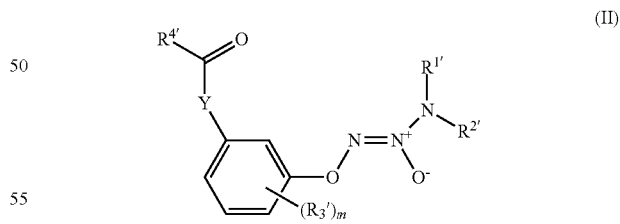

wherein
$R^{1'}$ and $R^{2'}$ are each independently selected from alkyl, alkyl substituted with alkoxy, acyloxy, OH, halo, or benzyl, alkenyl, and alkenyl substituted with alkoxy, acyloxy, OH, halo, or benzyl, or $R^{1'}$ and $R^{2'}$, together with the nitrogen atom to which they are bonded, form a heterocyclyl, e.g., heterocycloalkyl, having at least one or more heteroatoms selected from O, S and N;
$R^{3'}$ is independently selected from H, CN, NO₂, sulfonato, formyl, carboxy, mercapto, amido, amino, alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, wherein each of said alkyl, aryl alkyl, aryl, heterocycloalkyl, heteroaryl, heteroaryl alkyl, hydroxyalkyl, haloalkyl, aminoalkyl, alkoxy, aryloxy, alkylamino, and dialkylamino is optionally substituted with one or more substituents selected from alkyl, alkenyl, alkynyl, aryl alkyl, aryl, heterocycloalkyl, heteroaryl, heteroaryl alkyl, OH, hydroxyalkyl, halo, haloalkyl, aminoalkyl, alkoxy, aryloxy, thioalkoxy, acyl, acyloxy, alkoxycarbonyl, alkoxycarbonyloxy, alkylamino, and dialkylamino;

m is 0 to 4;

Y is a linker selected from the group consisting of —$NR^{9'}$—,

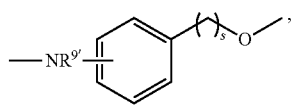

—S—, and —O—, wherein $R^{9'}$ is selected from the group consisting of H and $C_1$-$C_6$ alkyl, and s is 0 to 4;

$R^{4'}$ is a moiety selected from

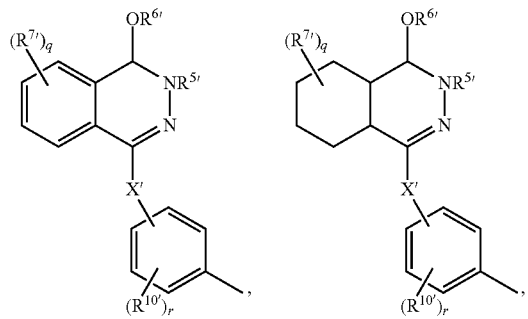

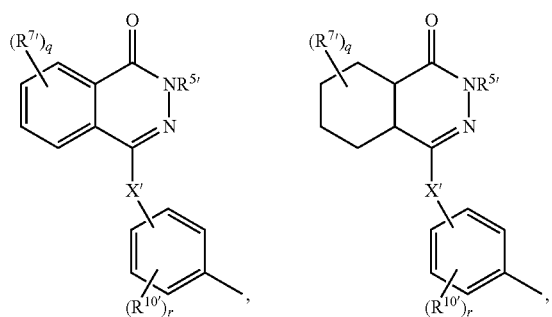

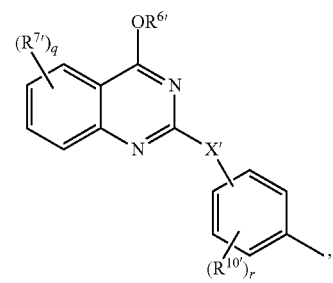

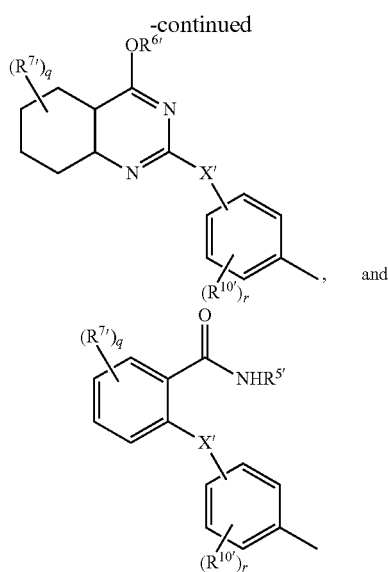

wherein $R^{5'}$ and $R^{6'}$ are each independently selected from H, acyl, and $C_{1-6}$ alkyl;

$R^{7'}$ is each independently selected from H, halo, $NO_2$, CN, OH, alkoxy, mercapto, thioalkoxy, amino, $C_{1-6}$ alkyl, $C_{2-7}$ haloalkyl, heterocycloalkyl, and aryl;

$R^{10'}$ is each independently selected from H, halo, OH, CN, $NO_2$, sulfonato, formyl, carboxy, mercapto, amido, amino, or an optionally substituted moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;

X' is a linker selected from $(CH_2)_r$—, —O—, —C(O)—, —O(CH_2)_r$—, —(CH_2)_rO$—, —S—, —S(CH_2)_r$—, —(CH_2)_rS$—, —$NR^{8'}$—, —(CH_2)_rNR^{8'}$—, $NR^{8'}(CH_2)_r$—, —$NR^{8'}C(O)NR^{8'}$—, and —$C(O)NR^{8'}C(O)$—; wherein r is 1 to 5; and $R^{8'}$ is selected from H and $C_1$-$C_6$ alkyl; and q and r are independently 0 to 4;

or a pharmaceutically acceptable salt thereof.

In certain embodiments, $R^{1'}$ and $R^{2'}$ are each individually selected from alkyl and alkyl substituted by alkoxy, acyloxy, OH, halo, or benzyl. In other embodiments, $R^{1'}$ and $R^{2'}$ join together with the nitrogen atom to which they are bonded to form a piperidinyl, pyrrolidinyl, piperazinyl, or morpholinyl.

In any of the foregoing embodiments or other embodiments, $R^{3'}$ is independently selected from H, CN, $NO_2$, sulfonato, formyl, carboxy, mercapto, amino, amino, alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, wherein each of said alkyl, aryl alkyl, aryl, heterocycloalkyl, heteroaryl, heteroaryl alkyl, hydroxyalkyl, haloalkyl, aminoalkyl, alkoxy, aryloxy, alkylamino, and dialkylamino is optionally substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino. In certain embodiments, $R^{3'}$ is H, CN, $NO_2$, carboxy, or an optionally substituted moiety selected from alkyl, aryl alkyl, aryl, heterocycloalkyl, heteroaryl, heteroaryl alkyl, hydroxyalkyl, haloalkyl, aminoalkyl, aryloxy, alkylamino, and dialkylamino. Preferably, $R^{3'}$ is $NO_2$.

In any of the foregoing embodiments or other embodiments, in is 0, 1, 2, or 3. Preferably, m is 2.

In any of the foregoing embodiments or other embodiments, Y is a linker selected from the group consisting of —$NR^{9'}$—, —S—, and —O—, wherein $R^{9'}$ is selected from the group consisting of H and $C_1$-$C_6$ alkyl. In certain embodiments, Y is —$NR^{9'}$- or —O—, wherein $R^{9'}$ is selected from H and $C_1$-$C_4$ alkyl. When Y

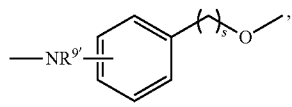

is either the amino or oxy terminus can be bonded to the carbonyl moiety of the compound of formula (II). Preferably, the oxy terminus is connected to the carbonyl. Furthermore, when Y is

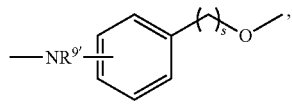

the —$NR^{9'}$-moiety can be at any suitable position on the phenyl ring (e.g., the 2-, 3-, 4-, 5-, or 6-position). In certain embodiments, the —$NR^{9'}$-moiety is attached to the phenyl ring at the 3- or 4-position.

In any of the foregoing embodiments or other embodiments, $R^{4'}$ is attached to the core structure of formula (II) at any suitable position on the phenyl ring (e.g., the 1-, 2-, 3-, 4- or 5-position). Similarly, the substituent(s) $R^{10'}$ are attached to the phenyl ring at any suitable position (e.g., the 1-, 2-, 3-, 4- or 5-position). The aryl, heteroaryl, or heterocycloalkyl moiety, connected via linker X', is attached at any suitable position to the phenyl ring (e.g., the 1-, 2-, 3-, 4- or 5-position). In certain embodiments, $R^{4'}$ is attached to the core structure of formula (II) at the 1-position on the phenyl ring. Additionally, $R^{10'}$ preferably is attached at the 2- and/or 4-positions, and the aryl, heteroaryl, or heterocycloalkyl moiety connected via linker X' is attached at the 5-position on the phenyl ring. Preferably, $R^{4'}$ is

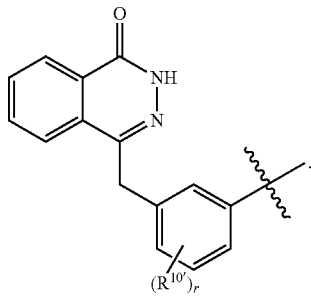

In any of the foregoing embodiments or other embodiments, $R^{7'}$ is H, OH, halo, or $C_{1-6}$ alkyl. Preferably, $R^{7'}$ is H or halo (e.g., F, Cl, Br). In any of the foregoing embodiments or other embodiments, $R^{10'}$ is H, OH, halo, or $C_{1-6}$ alkyl. Preferably, $R^{10'}$ is H or halo (e.g., F, Cl, Br). In any of the foregoing embodiments, r preferably is 0, 1, or 2.

Some groups in the definitions of the substituents in formulae (I) and (II), e.g., alkyl, alkenyl, aryl, or heterocyclyl, are optionally substituted with one or more moieties (e.g., 1 to 5, 1 to 4, 1 to 3, 1 or 2). Suitable substituents are selected from —[N(NO)O], halo, OH, alkylthio, arylthio, alkoxy, aryloxy, carboxy, carboxyalkyl, alkylcarboxy, amino, alkylamino, dialkylamino, nitroso, CN, sulfonato, mercapto, $NO_2$, oxo (=O), alkyl, alkenyl, cycloalkyl, heterocycloalkyl, aryl alkyl, aryl, benzylcarbonyl, phenylcarbonyl, phosphono, and phosphato. Preferred substituents are selected from halo, OH, alkoxy, amino, alkylamino, dialkylamino, CN, $NO_2$, alkyl, alkenyl, cycloalkyl, heterocycloalkyl, aryl alkyl, and aryl.

Specific examples of the compound of formula (I) include compounds a-d:

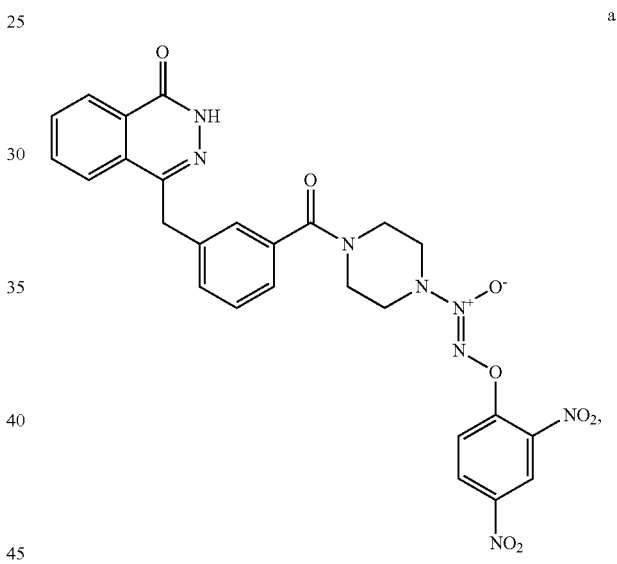

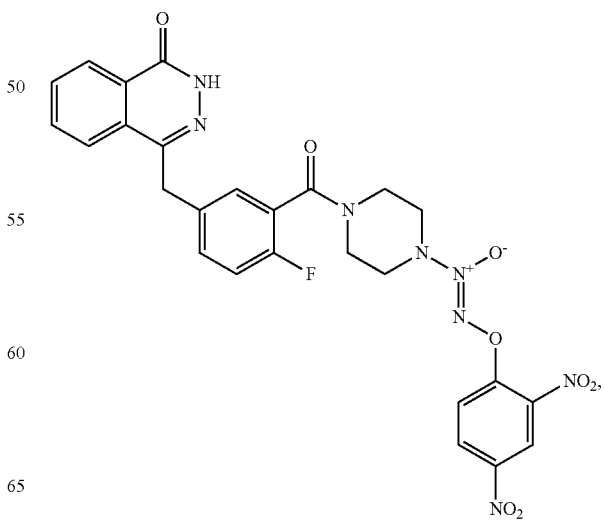

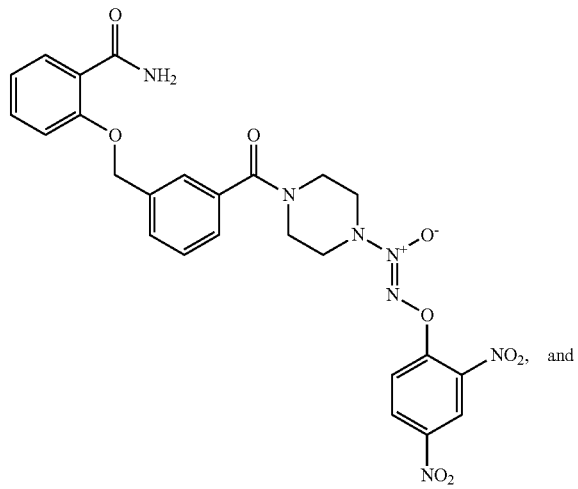
c
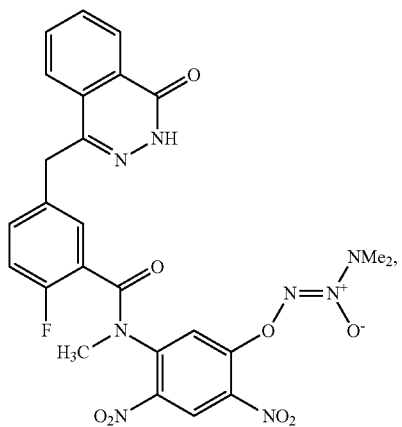
f
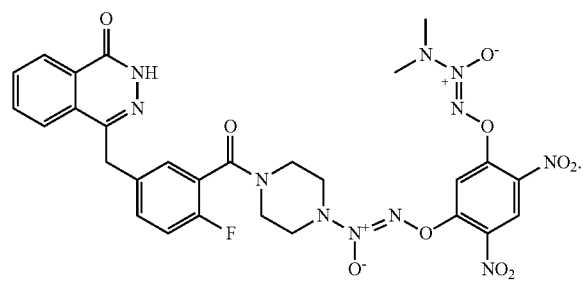
d
JS-65-103
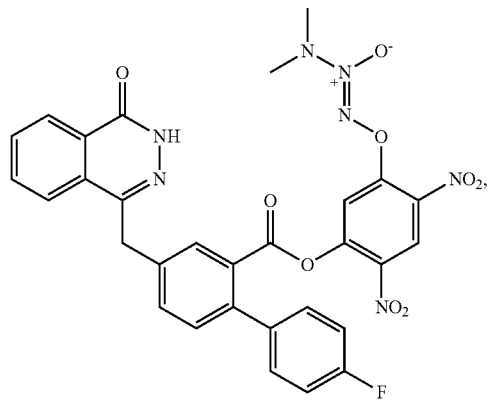
g
Specific examples of the compound of formula (II) include compounds e-i:
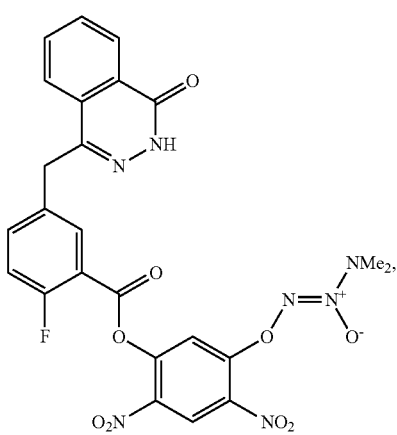
e
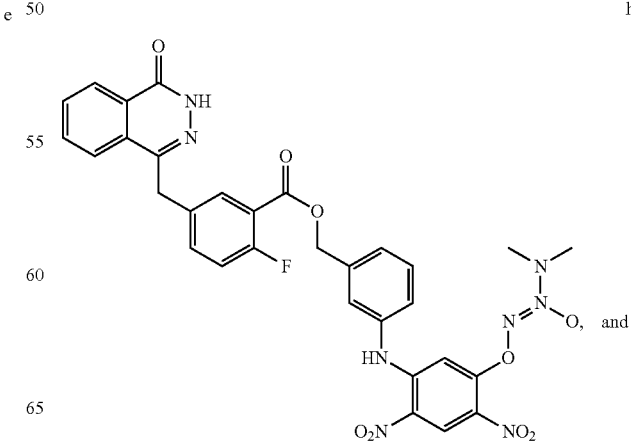
h -continued

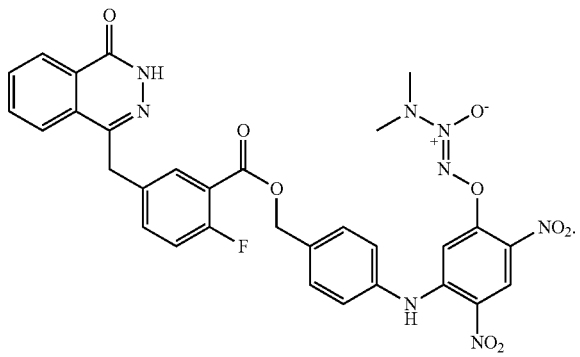

In any of the embodiments above, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. In accordance with an embodiment, the alkyl group is preferably a $C_1$-$C_3$ alkyl. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in hydroxyalkyl, haloalkyl including monohalo alkyl, dihalo alkyl, and trihalo alkyl, aminoalkyl, alkylamino, dialkylamino, etc.

In any of the embodiments above, the term "alkenyl," as used herein, means a linear alkenyl substituent containing from, for example, about 2 to about 12 carbon atoms (branched alkenyls are about 3 to about 12 carbons atoms), preferably from about 2 to about 8 carbon atoms (branched alkenyls are preferably from about 3 to about 8 carbon atoms), more preferably from about 3 to about 6 carbon atoms. In accordance with an embodiment, the alkenyl group is preferably a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like.

In any of the embodiments above, the term "alkynyl," as used herein, means a linear alkynyl substituent containing at least one carbon-carbon triple bond and from, for example, about 2 to about 12 carbon atoms (branched alkynyls are about 4 to about 12 carbons atoms), preferably from about 2 to about 8 carbon atoms (branched alkynyls are preferably from about 4 to about 8 carbon atoms), more preferably from about 3 to about 6 carbon atoms. Examples of such substituents include propynyl, propargyl, n-butynyl, pentynyl, isopentynyl, hexynyl, octynyl, dodecynyl, and the like.

In any of the embodiments above, the terms "hydroxy" and "thiol or mercapto" refer to the groups —OH and —SH, respectively.

In any of the embodiments above, the terms "alkoxy" and "thioalkoxy" embrace linear or branched alkyl groups that are attached to a divalent oxygen or sulfur, respectively. The alkyl group is the same as described herein. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. The term "aryloxy" refers to substituents that have an aryl group attached to divalent oxygen. The aryl group is the same as described herein. Examples of such substituents include phenoxy.

In any of the embodiments above, the term "halo" refers to a halogen selected from fluorine, chlorine, bromine, and iodine, preferably fluorine, chlorine, or bromine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ electrons, according to Hückel's Rule, wherein n=1, 2, or 3.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl.

In any of the embodiments above, the term "heterocyclyl" includes heterocycloalkyl and heteroaryl groups.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. Preferably, a heterocycloalkyl is a 5, 6, or 7-membered monocyclic ring and contains one, two, or three heteroatoms selected from nitrogen, oxygen, and/or sulfur. The heterocycloalkyl may be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl.

In any of the embodiments above, the term "aryl alkyl" as utilized herein means alkyl as defined herein, wherein at least one hydrogen atom is replaced with an aryl substituent as defined herein. Aryl alkyls include, for example, benzyl, phenethyl, and groups of the formula:

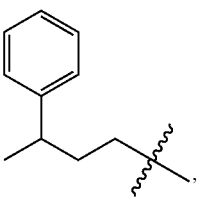 , 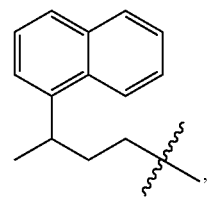 , and

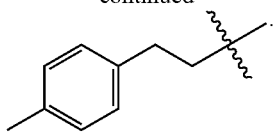

In any of the embodiments above, the term "alkylamino" refers to a secondary amine substituent with one hydrogen and one alkyl group directly attached to a trivalent nitrogen atom. The term "dialkylamino" refers to a tertiary amine substituent with two of the same or different alkyl groups directly attached to a trivalent nitrogen atom. The alkyl group is the same as described herein.

In any of the embodiments above, the term "carboxy" refers to the group —C(O)OH. The term "carboxyalkyl" refers to the group —RC(O)OH that is connected to the compound through the alkyl R group. The term "alkoxycarbonyl" refers to the group —C(O)OR, in which R is an alkyl group as described herein. The term "alkoxycarbonyloxy" refers to the group —OC(O)OR, in which R is an alkyl group as described herein. The term "formyl" refers to the group —C(O)H. The term "acyl" refers to the group —C(O)R and the teen "acyloxy" refers to the group —OC(O)R, in which R is an alkyl group as described herein.

In any of the embodiments above, the term "amido" refers to the group —C(O)NH$_2$.

In any of the embodiments above, the term "sulfonato" refers to the group —SO$_3$.

In any of the embodiments above, the alkyl, alkoxy, and alkylamino groups can be linear or branched. When an aryl group is substituted with a substituent, e.g., halo, amino, alkyl, OH, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

In any of the embodiments above, whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The diazeniumdiolated compounds of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

Nitric oxide release from the hybrid diazeniumdiolated compounds described herein can be determined/detected using known techniques such as those described in U.S. Pat. Nos. 6,511,991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide*, 6(2): 135-41 (2002); and Kitamura et al., "In vivo nitric oxide measurements using a microcoaxial electrode," *Methods Mol. Biol.*, 279: 35-44 (2004), which are incorporated herein by reference. In general, the amount of NO produced can be detected by a chemiluminescence method, electrochemical method, and/or an absorbance method. In addition, nitric oxide assay kits are commercially available.

The invention provides a pharmaceutical composition comprising the compound of formula (I) or (II) or a pharmaceutically acceptable salt thereof and a pharmaceutically acceptable carrier.

In the pharmaceutical compositions described herein, any suitable pharmaceutically acceptable carrier can be used, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. In one embodiment, the pharmaceutically acceptable carrier is a liquid that contains a buffer and a salt. The formulation can be presented in unit-dose or multi-dose sealed containers, such as ampoules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. In one embodiment, the pharmaceutically acceptable carrier is a buffered saline solution.

Further carriers include sustained-release preparations, such as semipermeable matrices of solid hydrophobic polymers containing the active agent, which matrices are in the form of shaped articles (e.g., films, liposomes, or microparticles).

The pharmaceutical composition can include carriers, thickeners, diluents, buffers, preservatives, surface active agents and the like. The pharmaceutical compositions can also include one or more additional active ingredients, such as antimicrobial agents, anti-inflammatory agents, anesthetics, and the like.

The pharmaceutical composition comprising the compound of formula (I) or (II) or a pharmaceutically acceptable salt thereof can be formulated for any suitable route of administration, depending on whether local or systemic treatment is desired, and on the area to be treated. The pharmaceutical composition can be formulated for parenteral administration, such as intravenous, intraperitoneal, intramuscular, or intratumoral injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

Desirably, the pharmaceutical composition also can be administered orally. Oral compositions can be in the form of powders or granules, suspensions or solutions in water or non-aqueous media, capsules, sachets, or tablets. Thickeners, flavorings, diluents, emulsifiers, dispersing aids, or binders may be desirable.

Suitable carriers and their formulations are further described in A. R. Gennaro, ed., *Remington: The Science and Practice of Pharmacy* (19th ed.), Mack Publishing Company, Easton, Pa. (1995).

The compound or a pharmaceutical composition comprising at least one compound of formula (I) or a pharmaceutically acceptable salt thereof can be administered in any suitable manner depending on whether local or systemic treatment is desired, and on the area to be treated. Desirably, the pharmaceutical composition is administered orally, but can be administered parenterally, most preferably by intravenous, intraperitoneal, intramuscular, or intratumoral injection. By the term "injecting," it is meant that the pharmaceutical composition is forcefully introduced into the target tissue. Although more than one route can be used to administer the pharmaceutical composition, a particular route can provide a more immediate and more effective reaction than another route. For regional delivery, the pharmaceutical composition can be administered intraarterially or intravenously, e.g., via the hepatic artery for delivery to the liver or the carotid artery for delivery to the brain.

The compound or a pharmaceutical composition comprising at least one compound of formula (I) or (II) or a pharmaceutically acceptable salt thereof can be administered in or on a device that allows controlled or sustained release of the compound of formula (I) or (II) or a pharmaceutically acceptable salt thereof, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the active agents. The pharmaceutical compositions of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid. Of course, administration of the compound or pharmaceutical composition can be accomplished via any route that efficiently delivers the active agents to the target tissue.

The inventive methods comprise administering an effective amount of a compound of formula (I) or (II) or a pharmaceutically acceptable salt thereof. An "effective amount" means an amount sufficient to show a meaningful benefit in an individual, e.g., promoting at least one aspect of tumor cell cytotoxicity, or treatment, healing, prevention, delay of onset, halting, or amelioration of other relevant medical condition(s) associated with a particular cancer. Preferably, one or more symptoms of the cancer are prevented, reduced, halted, or eliminated subsequent to administration of a compound of formula (I) or (II) or a pharmaceutically acceptable salt thereof, thereby effectively treating the cancer to at least some degree.

Effective amounts may vary depending upon the biological effect desired in the individual, condition to be treated, and/or the specific characteristics of the compound of formula (I) or (II) or a pharmaceutically acceptable salt thereof, and the individual. In this respect, any suitable dose of the compound of formula (I) or (II) or a pharmaceutically acceptable salt thereof can be administered to the patient (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or (II) or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (II) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

Reactive Oxygen Species (ROS) are derived from the metabolic reduction of molecular oxygen. ROS include the superoxide anion radical ($O_2^-$), singlet oxygen ($^1O_2$), hydrogen peroxide ($H_2O_2$), and the highly reactive hydroxy radical ($^-OH$). These species are highly toxic. ROS normally exist in all aerobic cells in balance with biochemical antioxidants. However, oxidative stress disrupts the critical balance because of excess ROS and/or antioxidant depletion. ROS can cause tissue damage by reacting with lipids in cellular membranes, nucleotides in DNA, sulfhydryl groups in proteins, and crosslinking/fragmentation of ribonucleoproteins. Damage to DNA by ROS is a major cause of cancer. ROS can damage DNA and the division of cells with unpaired or misrepaired damage leads to mutations. The majority of mutations induced by ROS appear to involve modification of guanine, causing G→T transversions. If it relates to critical genes such as oncogenes or tumor suppressor genes, initiation/progression can result. ROS can act at several steps in a multistate carcinogenesis. Cells characterized by increased ROS levels often have depressed levels of antioxidant enzymes.

ROS are also generated when cancer patients are treated with certain chemotherapeutic agents. For example, ROS generation and mitochondrial dysfunction are thought to be involved in the apoptotic response of human H460 NSCLC cancer cells when treated with a proteasome inhibitor, bortezomib.

A major product of ROS attack in genomic DNA is the premutagenic lesion 7,8-dihydro-8-oxoguanine (8-oxoG), which causes G-to-T transversions. The main defense against the 8-oxoG is the base excision repair (BER) pathway, which in eukaryotes is initiated by the OGG1 protein, a DNA glycosylase that catalyzes the excision of 8-oxodG from DNA. OGG1 is responsible for over 95% of BER activity in mammalian cells. A correlation between OGG1 protein expression levels and $IC_{50}$ values for the compound of formula (I) has been surprisingly discovered. In particular, the compound of formula (I) is less toxic in the cell lines expressing high levels of OGG1 protein. This establishes OGG1 as a potential marker for sensitivity. As a result, in the inventive methods the cancer cell can have an 8-oxo-dG DNA glycosylase (OGG1) content less than about 25 units (e.g., less than about 20 units, less than about 15 units, less than about 10 units, or less than about 5 units) relative to the OGG1 content of the nonmalignant lung epithelial HPL1D which is 100 units.

The amount of OGG1 in a particular cancer cell can be determined by assays known in the art using, for example, an enzyme-linked immunosorbent assay (ELISA), real-time PCR (RT-PCR), and/or Western blot analysis. For example, commercially available kits can be used to determine the amount of OGG1 in a cell (e.g., an OGG1 assay kit).

It has been discovered that the PARP-inhibitor/NO-donor dual prodrugs of formula (I), formula (II), or a pharmaceutically acceptable salt thereof can effectively kill NSCLC cells, as evaluated by inhibition of cell proliferation, modulation of DNA damage/repair, and apoptosis. Therefore, it is envisioned that the compounds described herein have clinical applications as "stand alone" therapeutics against cancer cells, particularly cancer cells characterized by high endogenous levels of ROS and/or low levels of DNA repair protein OGG1. The inventive compounds described herein also can serve as adjunct chemosensitizing agents in a wide variety of cancers.

Cancers treatable with the methods described herein include tumors associated with the oral cavity (e.g., the tongue and tissues of the mouth) and pharynx, the digestive system (e.g., the esophagus, stomach, small intestine, colon, rectum, anus, liver, gall bladder, and pancreas), the respiratory system (e.g., the larynx, lung, and bronchus), bones and joints (e.g., bony metastases), soft tissue, the skin (e.g., melanoma and squamous cell carcinoma), breast, the genital system (e.g., the uterine cervix, uterine corpus, ovary, vulva, vagina, prostate, testis, and penis), the urinary system (e.g., the urinary bladder, kidney, renal pelvis, and ureter), the eye and orbit, the brain and nervous system (e.g., glioma), and the endocrine system (e.g., thyroid). The target tissue also can be located in lymphatic or hematopoietic tissues. For example, the tumor can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). The tumor to be treated is not necessarily the primary tumor. Indeed, the tumor can be a metastasis of a primary tumor located in a different tissue or organ.

Specific examples of cancers treatable with the present methods include, without limitation, acute lymphoblastic leukemia, acute myeloid leukemia, adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, chronic lymphocytic, leukemia, chronic myelogenous leukemia, liver cancer, non-small cell lung cancer, small cell lung cancer, Hodgkin's disease, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/ plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous T-cell lymphoma, testicular cancer, malignant thymoma, thyroid cancer, gestational trophoblastic tumor, urethral cancer, uterine sarcoma, vaginal cancer, vulvar cancer, and Wilms' tumor.

The cancers that will be treatable by the methods of the present invention include, without limitation, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In an embodiment of the methods of the invention, the cancer is leukemia, melanoma, lung cancer, colon cancer, brain cancer, ovarian cancer, breast cancer, prostate cancer, or renal cancer. Preferably, the cancer is non-small cell lung cancer, such as cells having one or more characteristics of H1703, H1734, H1693, H1568, H1373, H2030, H2023, and H1944 cells. In an embodiment, the NSCLC cell can have one or more of the following characteristics:

| Cell line | ROS | OGG1 |
|---|---|---|
| H1703 | 22.0 | 14 |
| H1734 | 18.4 | 103 |
| H1693 | 15.1 | 0.5 |

Preferably, the NSCLC cell has the characteristics of an H1703 or H1693 cell line. These NSCLC cell lines can be distinguished from other lung cancer cell lines, which have one or more biomarkers outside of the desirable range. For example:

| Cell line | ROS | OGG1 |
|---|---|---|
| H441 | 14.7 | 28 |
| A549 | 2.3 | 260 |
| H1395 | 8.2 | 106 |
| H838 | 6.9 | 204 |

Differential NSCLC cells' responsiveness to the drug is believed to be related to the cancer cells' endogenous level of reactive oxygen species (ROS). The level of endogenous ROS correlates significantly with the drug toxicity measured as $IC_{50}$ values. Therefore, it is envisioned that a compound of formula (I) or (II) or a pharmaceutically acceptable salt thereof shows a synergistic effect with therapeutics acting through generation of ROS.

In certain embodiments of the invention, the compound of formula (I) or (II) or a pharmaceutically acceptable salt thereof can be co-administered with a chemotherapeutic agent. In an embodiment, the chemotherapeutic agent produces reactive oxygen species (ROS) in the cancer cell. In this regard, the present invention is directed a pharmaceutical composition comprising a pharmaceutically acceptable carrier and a combination of the compound of formula (I) or (II) or a pharmaceutically acceptable salt thereof and a chemotherapeutic agent. The cancer cell is the same as described herein.

Examples of chemotherapeutic agents, including agents that may produce ROS, include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

In an embodiment, the chemotherapeutic agent that produces ROS is an antitumor antibiotic or a proteosome inhibitor, e.g., doxorubicin or bortezomib.

Alternatively, the compound of formula (I) or (II) or a pharmaceutically acceptable salt thereof can be co-administered with a high energy radiation that produces ROS.

For purposes of the present invention, the term "patient" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The following examples further illustrate the invention but, of course, should not be construed as in any way limiting its scope.

EXAMPLES

Starting materials were purchased from Aldrich Chemical Co. (Milwaukee, Wis.) unless otherwise indicated. NMR spectra were recorded on a Varian UNITY INOVA™ spectrometer; chemical shifts (δ) are reported in parts per million (ppm) downfield from tetramethylsilane. Ultraviolet (UV) spectra were recorded on an Agilent Model 8453 or a Hewlett-Packard model 8451A diode array spectrophotometer. Elemental analyses were performed by Midwest Microlab (Indianapolis, Ind.). Nitric oxide measurements were performed using a SIEVERS™ Nitric Oxide Analyzer (NOA), model 280i (Instruments Business Group, Boulder, Colo.). Chromatography was performed on a Biotage SP1™ FLASH™ Purification System. Prepacked silica gel flash chromatography columns were purchased from Silicycle (Quebec City, Canada) or from Yanazen Science Inc. (San Bruno, Calif.).

Example 1

Figure 2:
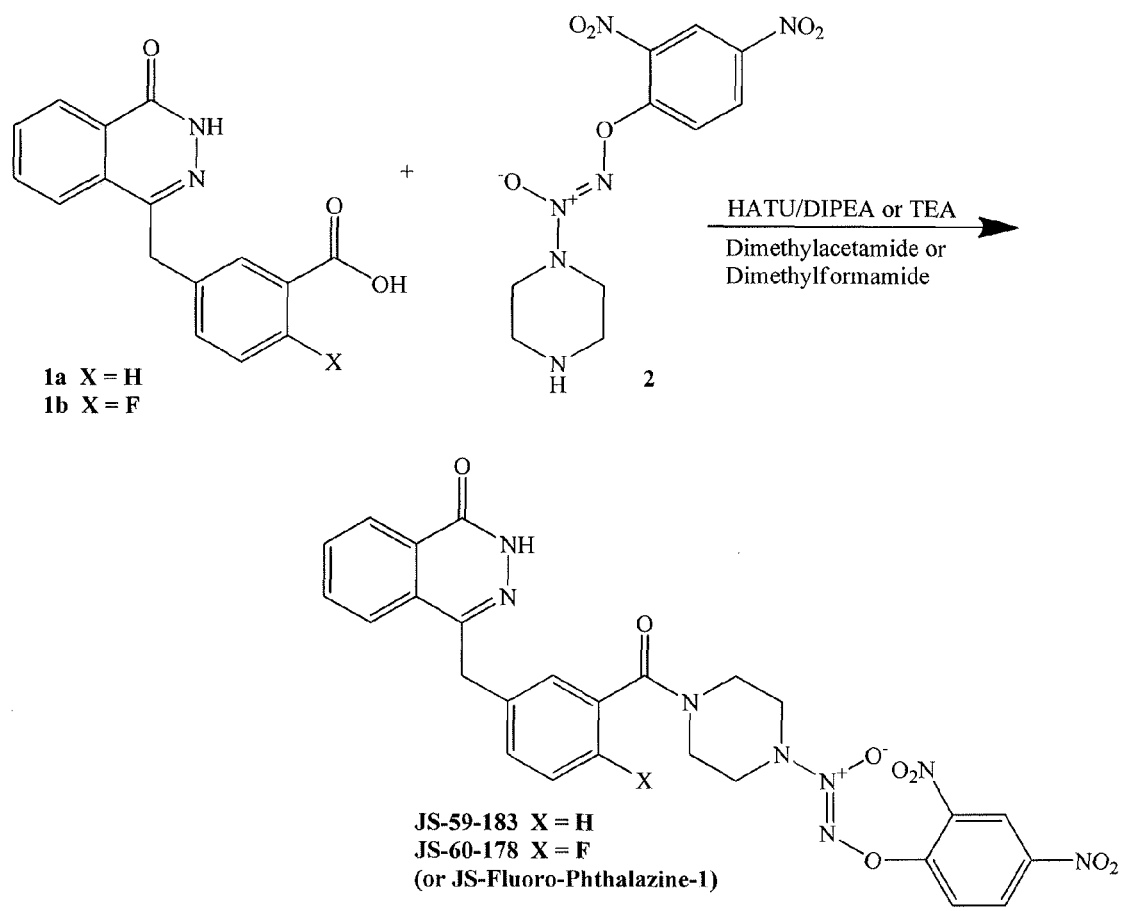
FIG. 2 depicts a reaction scheme illustrating the synthesis of compounds in accordance with an embodiment of the invention: JS-59-183 and JS-60-178.

This example demonstrates the synthesis of 2,4-dinitrophenyl 4-[5-[(4-oxo-3H-phthalazin-1-yl)methyl]-benzoyl]piperazine-1-yl-1-ium-1,2-diolate (JS-59-183) in an embodiment of the invention. See FIG. 2.

3-[(4-Oxo-3H-phthalazin-1-yl)methyl]benzoic acid, 1a, was prepared as described by Menear et al. (*J. Med. Chem.*, 51: 6581-6591 (2008)). To a slurry of 557 mg (1.6 mmol) of the hydrochloride salt of $O^2$-(2,4-dinitrophenyl) 1-(piperazine-1-yl)diazene-1-ium-1,2-diolate, 2 (Shami et al., *J. Med. Chem.*, 49: 4356-4366 (2006)), 448 mg (1.6 mmol) of 1a and 608 mg (1.6 mmol) of ((2-(7-aza-1H-benzotriazole-1-yl)-1,1,3,3-tetramethyluronium hexafluorophosphate) (HATU) in 5 mL of dimethylacetamide was added 1.02 mL (6 mmol) of diisopropyl ethylamine. The resulting solution was stirred at room temperature for 1 h, followed by the addition of 40 mL of water. The resulting precipitate was collected by filtration and recrystallized from ethanol giving 827 mg of an off-white solid: uv (acetonitrile), $\lambda_{max}$ 294 nm ($\epsilon$=18.9 mM$^{-1}$ cm$^{-1}$); mp 114-17° C.; $^1$H NMR (DMSO-d$_6$), δ 3.63-3.68 (m, 8H), 4.38 (s, 2H), 7.28-7.30 (m, 1H), 7.39-7.46 (m, 3H), 7.81-7.98 (m, 4H), 8.26 (d, 1H) J=7.42 Hz, 8.56-8.59 (dd, 1H) J=2.7, 7.42 Hz, 8.88 (d, 1H) J=2.7 Hz, 12.06 (s, 1H).

Example 2

This example demonstrates the synthesis of 2,4-dinitrophenyl 4-[2-fluoro-5-[(4-oxo-3H-phthalazin-1-yl)methyl]-benzoyl]piperazine-1-yl-1-ium-1,2-diolate (JS-60-178) in an embodiment of the invention. See FIG. 2.

To a mixture of 167 mg (0.560 mmol) of 2-fluoro-5-[(4-oxo-3H-phthalazin-1-yl)methyl]benzoic acid, 1b, 209 mg (0.6 mmol) of the hydrochloride salt of $O^2$-(2,4-dinitrophenyl) 1-(piperazine-1-yl)diazen-1-ium-1,2-diolate, 2 (Shami et al., *J. Med. Chem.*, 49: 4356-4366 (2006)), and 247 mg of HATU, were added 0.247 mL (1.8 mmol) of triethylamine and 5 mL of dimethylformamide; the resulting solution was stirred overnight. Water (5 mL) was added to the reaction mixture, which was stirred at room temperature for 1 h. The resulting yellow precipitate was collected by filtration and the solid was washed with ice-cold 1:1 water:DMF, then allowed to dry to give 264 mg of a yellow solid. The material was recrystallized from methanol:dichloromethane:ether: uv, (acetonitrile), $\lambda_{max}$ 295 nm ($\epsilon$=20.5 mM$^{-1}$ cm$^{-1}$); mp 150-3, $^1$H NMR (DMSO-d$_6$), δ 3.41 (b, 1H), 3.58 (b, 1H), 3.72 (b, 1H), 3.84 (b, 1H), 4.33 (s, 2H), 7.25 (t, 1H) J=9 Hz, 7.37-7.46 (m, 2H), 7.82 (t, 2H) J=9 Hz, 7.87-7.97 (m, 3H), 8.24 (d, 1H) J=7.8 Hz, 8.54-8.57 (dd, 1H) J=2.4, 7.8 Hz, 8.86 9 (d, 1H) J=2.4 Hz, 12.58 (s, 1H).

Example 3

Figure 3:
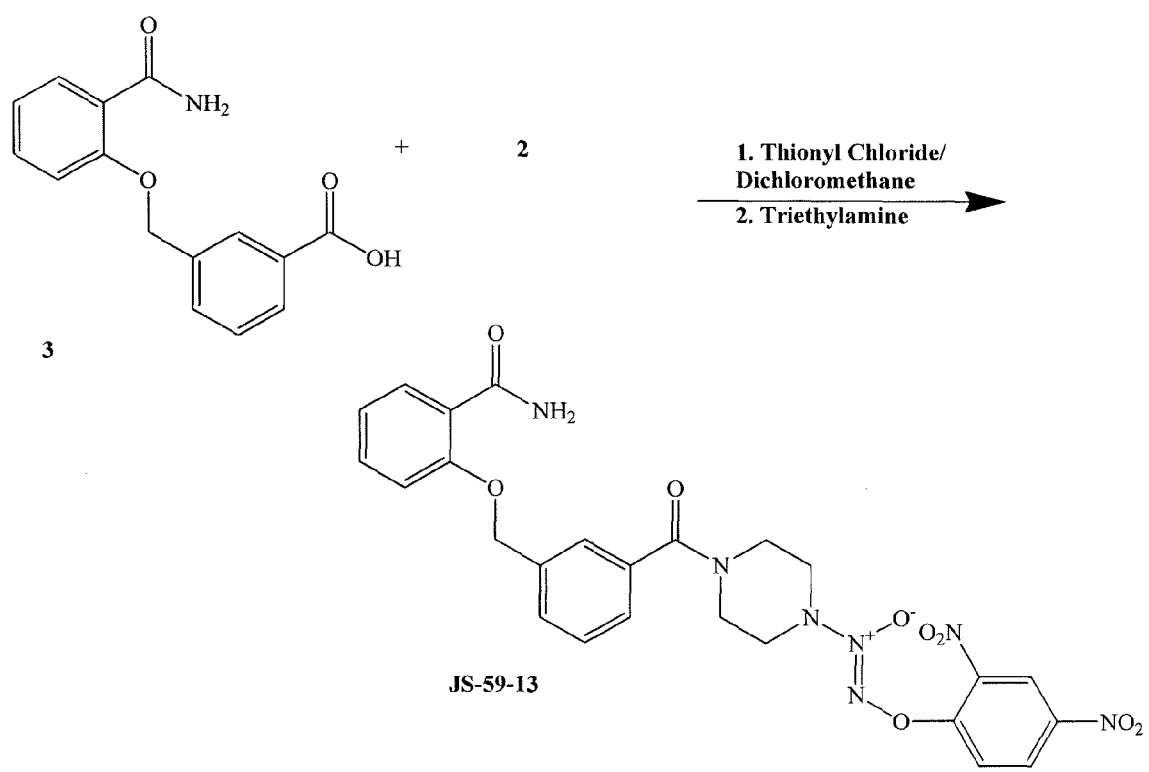
FIG. 3 depicts a reaction scheme illustrating the synthesis of a compound in accordance with an embodiment of the invention: JS-59-13.

This example demonstrates the synthesis of 2,4-dinitrophenyl 4-[2-benzyloxy benzamide]piperazine-1-yl-1-ium-1,2-diolate (JS-59-13) in an embodiment of the invention. See FIG. 3.

To a slurry of 245 mg (0.904 mmol) of 2-[(1-carboxy)benzyloxy]benzamide, 3, prepared as described by Menear et al. (*Bioorg. Med. Chem. Lett.*, 18: 3942-3945 (2008)), in 10 mL of dimethylformamide was added 0.100 mL of thionyl chloride and stirred at room temperature for 30 min. To the reaction mixture were added 313 mg (0.9 mmol) of the hydrochloride salt of 2 and 0.5 mL of triethylamine. After stirring overnight, water was added. The solid product was extracted with dichloromethane and washed with dilute sodium bicarbonate solution, dried over sodium sulfate filtered through magnesium sulfate and evaporated to give 298 mg of a solid. The product was chromatographed on silica gel, eluted with 9:1 dichloromethane:methanol: uv, (acetonitrile), $\lambda_{max}$ 298 nm ($\epsilon$=000 mM$^{-1}$ cm$^{-1}$); mp 110-111° C.; $^1$H NMR (DMSO-d$_6$), δ 3.73 (b, 8H), 5.35 (s, 2H), 7.12 (t, 2H) J=7.8 Hz, 7.35 (d, 1H) J=8.4 Hz, 7.44-7.62 (m, 4H), 7.69 (t, 1H) J=8.4 Hz, 7.76 (d, 1H) J=7.8 Hz, 7.94 (d, 1H) J=9 Hz, 8.55 (dd, 1H) J=2.73, 9.0 Hz, 8.80 (d, 1H) J=2.73 Hz; $^{13}$C NMR (DMSO d$_6$), δ 50.29, 70.04, 101.27. 113.98, 116.8, 118.5, 121.88, 127.22, 126.56, 127.31, 129.30, 129.37, 130.13, 134.21, 135.52, 135.78, 136.95, 137.29, 142.62, 153.16, 160.16, 169.26. Anal., C, H, N: Calcd. for $C_{25}H_{27}N_7O_9$: C, 53.10; H, 4.10; N, 17.34. Found: C, 53.80; H, 4.11; N, 17.47.

Example 4

This example demonstrates the synthesis of 1-[1-(N,N-dimethylamino)diazen-1-ium-1,2-diol-2-ato]-2,4-dinitrophenyl 4-[2-fluoro-5-[(4-oxo-3H-phthalazin-1-yl)methyl]-benzoyl]piperazine-1-yl-1-ium-1,2-diolate (JS-65-103) in an embodiment of the invention.

To a solution of 24 mg (0.08 mmol) of 2-fluoro-5-[(4-oxo-3H-phthalazin-1-yl)methyl]benzoic acid (Menear et al., *J. Med. Chem.*, 51: 6581-6591 (2008)) and 30 mg (0.08 mmol) of 2-(7-aza-1H-benzotriazole-1-yl)-1,1,3,3-tetramethyluronium hexafluorophosphate (HATU) in 2.5 mL of N,N-dimethylformamide was added 31 μL (0.18 mmol) of diisopropyl ethylamine (DIPEA). To the solution was gradually added 36 mg (0.08 mmol) of the hydrochloride salt in 2.5 mL of N,N-dimethylformamide and the resulting solution was stirred at room temperature overnight. The solution was treated with 10 mL of water, and the resulting slurry was stirred for 1 hr, centrifuged, and the liquid decanted. The precipitate was washed with water, then extracted with ethyl acetate and washed with 5% sodium bicarbonate. The organic layer was dried over sodium sulfate, filtered through a layer of magnesium sulfate, and concentrated under vacuum to give 31 mg of a beige solid (JS-65-103): uv (0.2% DMSO/ethanol), $\lambda_{max}$ 287 nm ($\epsilon$=32 mM$^{-1}$ cm$^{-1}$); $^1$H NMR (acetone-d$_6$), δ 3.30 (s, 6H), 3.58-3.97 (m, 8H), 7.14-7.22 (m, 1H), 7.44-7.54 (m, 2H), 7.79 (s, 1H), 7.80-7.88 (m, 1H), 7.94-7.96 (m, 2H), 8.32-8.34 (m, 1H), 8.86 (s, 1H), 11.75 (s, 1H); $^{13}$C NMR (acetone-d$_6$) δ 37.91, 41.76, 50.93, 51.24, 105.37, 116.64, 116.85, 124.55, 124.73, 126.1, 126.31, 127.31, 129.49, 130.19, 130.45, 132.1, 132.23, 132.34, 132.80, 134.22, 145.74, 154.8, 155.2, 160.44, 165.15.

The material contained impurities from N,N-dimethylformamide, dichloromethane, and other minor impurities. For further decomposition and biological screening, a portion of the compound was purified on a Phenomenex LUNA™ C18 column, 3 μm, 150×2.0 mm, with a gradient consisting of water and acetonitrile containing 0.1% formic acid. HRMS (ESI) m/z calculated for $C_{28}H_{27}FN_{11}O_{10}$ [M+H]$^+$ 696.19209. found 696.19276.

Example 5

This example demonstrates the determination of intracellular reactive oxygen/nitrogen species and nitric oxide of specific compounds of formula (I) in an embodiment of the invention.

Intracellular level of reactive oxygen/nitrogen species was quantified by the oxidation of the ROS/RNS-sensitive fluorophore 5-(and-6)-chloromethyl-2',7'-dichlorodihydrofluorescein diacetate (Invitrogen, Carlsbad, Calif.). Cells growing on six-well plates (6×10$^5$/well) were loaded with 5 μM 5-(and-6)-chloromethyl-2',7'-dichlorodihydrofluorescein diacetate in Hanks' balanced salt solution (HBSS) at 37° C. and 5% $CO_2$. After 30 min of incubation, HBSS containing the probe was removed, cells were rinsed with HBSS, and 3 ml of fresh HBSS was added to each well followed by the addition of compounds (10 μM) or DMSO as a control. After 60 min, the cells were collected by scraping in HBSS, and 2',7'-dichlorofluorescein (DCF) fluorescence was measured by using a PerkinElmer Life and Analytical Sciences (Waltham, Mass.) LS50B luminescence spectrometer with the excitation source at 488 nm and emission at 530 nm.

The intracellular level of nitric oxide after treatment with the compounds JS-59-183 or JS-60-178 was quantified by using the NO-sensitive fluorophore 4-amino-5-methylamino-2,7 difluorofluorescein (DAF-FM) diacetate (Invitrogen, Carlsbad, Calif.). Cells growing on six-well plates were loaded with 2.5 μM DAF-FM diacetate in HBSS at 37° C. and 5% $CO_2$. After 30 min of incubation, the cells were rinsed with HBSS to remove excess probe, and compounds in fresh HBSS was added to the cells at 10 μM final concentration. After 30 min incubation, the fluorescence of the benzotriazole derivative formed on DAF-FM's reaction with aerobic NO was analyzed by using a PerkinElmer Life and Analytical Sciences LS50B luminescence spectrometer with the excitation source at 495 nm and emission at 515 nm. All experiments were performed at least three times, each time at least in triplicate.

Figure 4A:
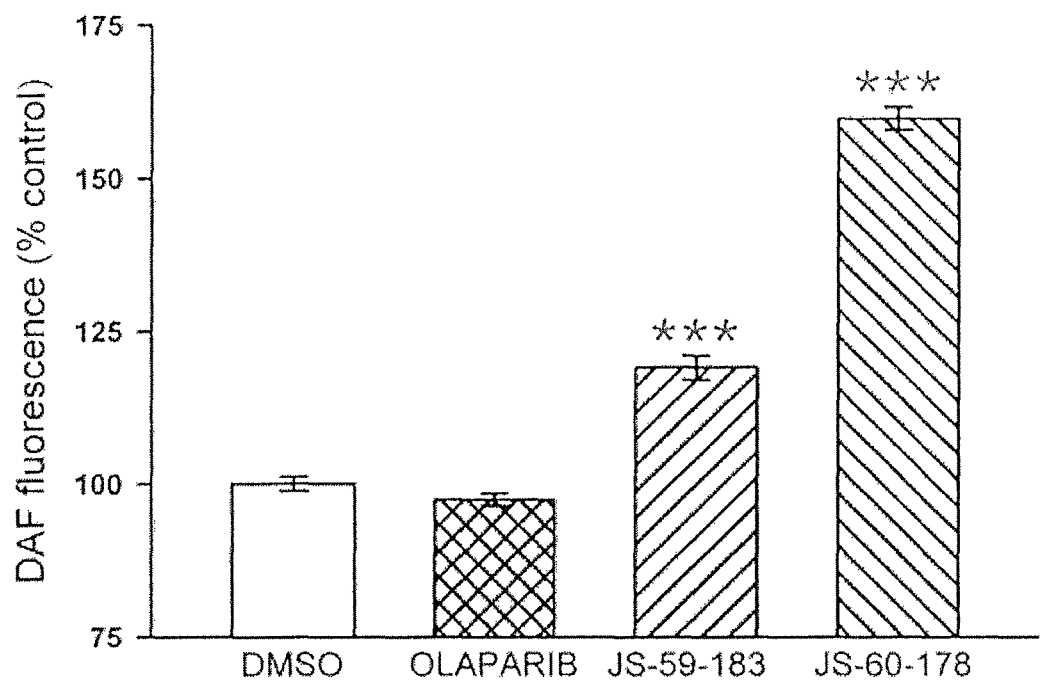
FIG. 4A depicts the intracellular NO release from JS-59-183 and JS-60-178 in H1703 lung adenocarcinoma cells measured as DAF fluorescence.
Figure 4B:
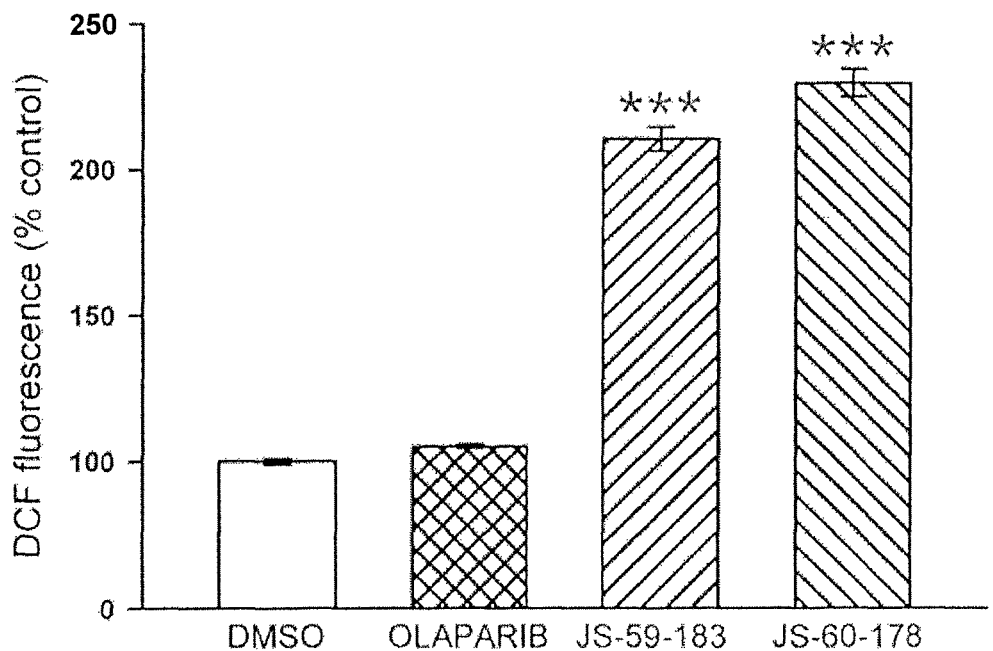
FIG. 4B depicts illustrating the intracellular ROS/RNS level of JS-59-183 and JS-60-178 measured as DCF fluorescence. (n=8); ***P<0.0001, by paired t test, compared with cells treated with DMSO only.

These assays demonstrate that the PARP-inhibitor/NO-donor dual prodrugs JS-59-183 and JS-60-178 are cell permeable and decompose within the cell releasing NO (FIG. 4A), as demonstrated with NO-specific reagent DAF-FM diacetate. There was also an increase in ROS generation after treatment with JS-59-183 and JS-60-178, as detected by the oxidation-sensitive fluorophore DCF (FIG. 4B).

Example 6

This example demonstrates the inhibition of PARP of specific compounds of formula (I) in an embodiment of the invention.

PARP enzyme inhibition was measured using HT Universal Colorimetric 96-well PARP assay kit (Trevigen, Gaithersburg, Md.), according to manufacturer's protocol with small modifications. GSH (1 mM final concentration) was added to the wells containing inhibitors, to allow activation of the prodrugs. The absorbance at 450 nm was measured.

Figure 5:
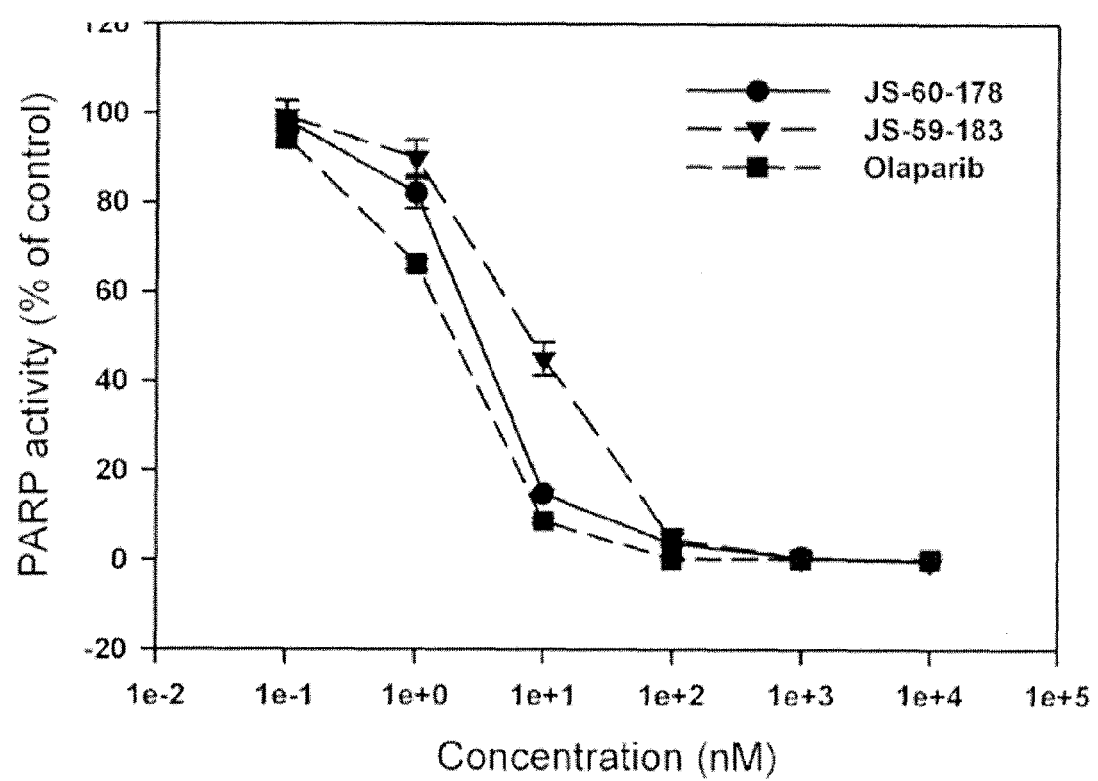
FIG. 5 depicts inhibition curves of PARP enzyme by JS-60-178 (●) and JS-59-183 (▼), compared with Olaparib (■). The inhibitors were tested in concentration range of 0.1 nM-10 μM.

The PARP inhibitory activities of JS-59-183 and JS-60-178 were comparable to that of Olaparib. PARP enzyme IC$_{50}$ values estimated for JS-60-178 were 2.9 nM, for JS-59-183 8.25 nM, and for Olaparib 2.0 nM (FIG. 5).

Example 7

This example demonstrates the inhibition of cell proliferation of specific compounds of formula (I) in an embodiment of the invention.

Cell lines were obtained from the American Type Culture Collection (Manassas, Va.) and cultured according to the supplier's protocol. For proliferation assays cells were seeded at 1×10$^4$ per well (H1693, H322M, H1703, H1944, H1355, H2122, H441, H1568) or 5×10$^3$ per well (H460, H1792, A549, H2023, H2030, H23) in 96-well plates and allowed to adhere for 24 h. Compounds were prepared as 10 mM stock solutions in DMSO. Increasing drug concentrations in 10 μl of PBS were added to 100 μl of the culture medium for 72 h. MTT assay (Promega, Madison, Wis.) was performed according to the manufacturer's protocol. Each concentration was represented in six repeats, and the screening was performed as at least two independent experiments. IC$_{50}$ values were calculated by using Sigma Plot software (Systat Software, Inc., San Jose, Calif.).

JS-59-183 and JS-60-178 inhibited growth of NSCLC cell lines with IC$_{50}$ concentrations ranging from 3 to 20 μM. Both IC$_{50}$ and total growth inhibition (TGI) values for JS-59-183 and JS-60-178 were lower than those of Olaparib for the most sensitive cell lines, suggesting that NO released from the prodrug upon activation with GSH contributes to the cytotoxicity. See Table 1.

TABLE 1

| | JS-60-178 | | JS-59-183 | | Olaparib | |
|---|---|---|---|---|---|---|
| Cell line | IC$_{50}$ [μM] | TGI [μM] | IC$_{50}$ [μM] | TGI [μM] | IC$_{50}$ [μM] | TGI [μM] |
| H1568 | 3.0 | 4.0 | 6.5 | 9.0 | 36 | 113 |
| H1703 | 4.3 | 6.7 | 6.8 | 11.2 | 20 | 60 |
| H441 | 4.5 | 6.2 | 8.1 | 11.7 | 28 | 84 |
| H1693 | 5.4 | 6.6 | 5.3 | 7.3 | 19 | 65 |
| H2122 | 7.5 | 11.0 | 11.2 | 25.0 | 38 | 140 |
| H322M | 7.9 | 11.6 | 9.0 | 14.0 | 50 | 360 |
| H1355 | 8.2 | 15.0 | 11.4 | 23.0 | 33 | 113 |
| H23 | 8.4 | 12.3 | 7.5 | 15.2 | 10 | 70 |
| H2030 | 9.2 | 15.2 | 13.8 | 25.0 | 34 | 117 |
| H1944 | 10.5 | 19.0 | 14.0 | 28.0 | 25 | 88 |
| H1792 | 12.7 | 19.0 | 14.0 | 20.0 | 16 | 38 |

TABLE 1-continued

| | JS-60-178 | | JS-59-183 | | Olaparib | |
|---|---|---|---|---|---|---|
| Cell line | IC$_{50}$ [μM] | TGI [μM] | IC$_{50}$ [μM] | TGI [μM] | IC$_{50}$ [μM] | TGI [μM] |
| A549 | 13.5 | 22.0 | 16.8 | 26.0 | 28 | 100 |
| H2023 | 15.0 | 25.0 | 19.4 | 32.5 | 20 | 85 |
| H460 | 16.4 | 24.0 | 13.8 | 24.8 | 12 | 37 |

Figures 6A, 6B:
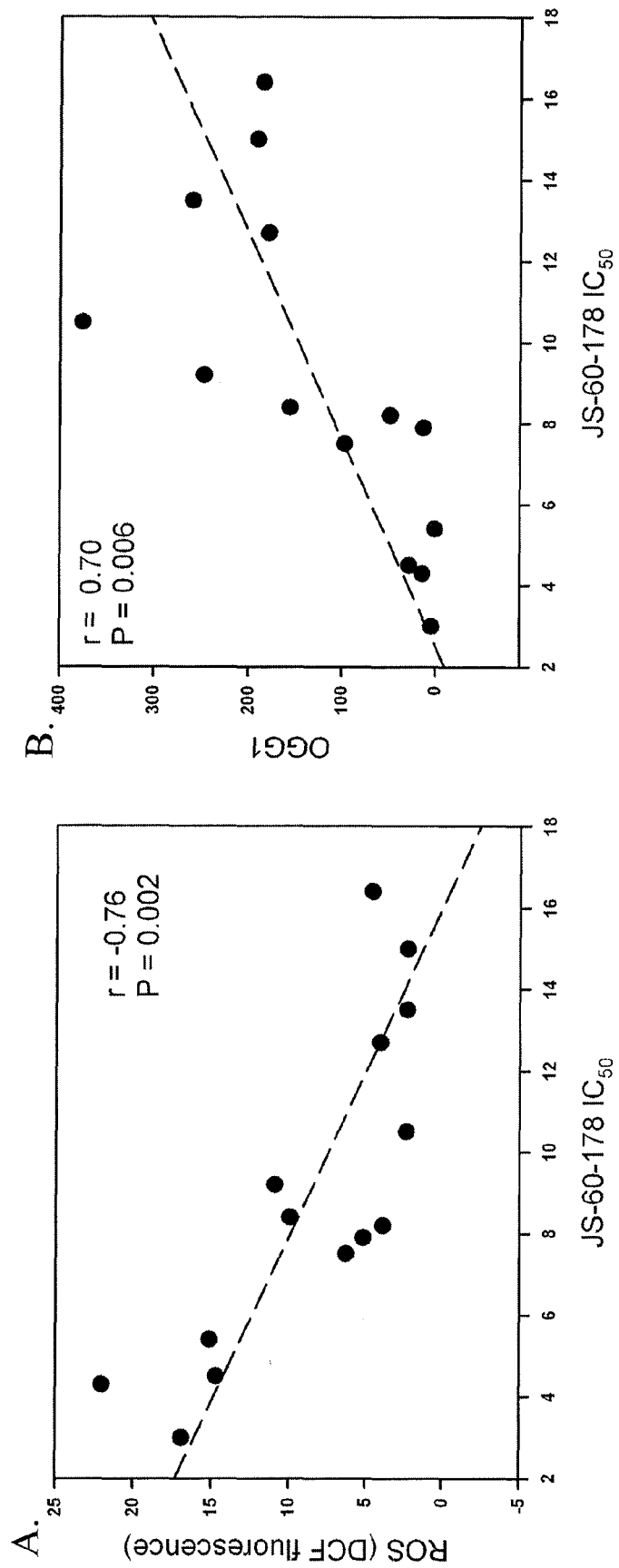
FIG. 6 is a series of graphs depicting the toxicity (expressed as $IC_{50}$ and TGI) of JS-60-178 correlated with levels of endogenous ROS/RNS (measured as DCF fluorescence), with levels of DNA repair protein OGG1, and with levels of ROS/RNS scavenger peroxiredoxin 1 (PRX1).
Figures 6C, 6D:
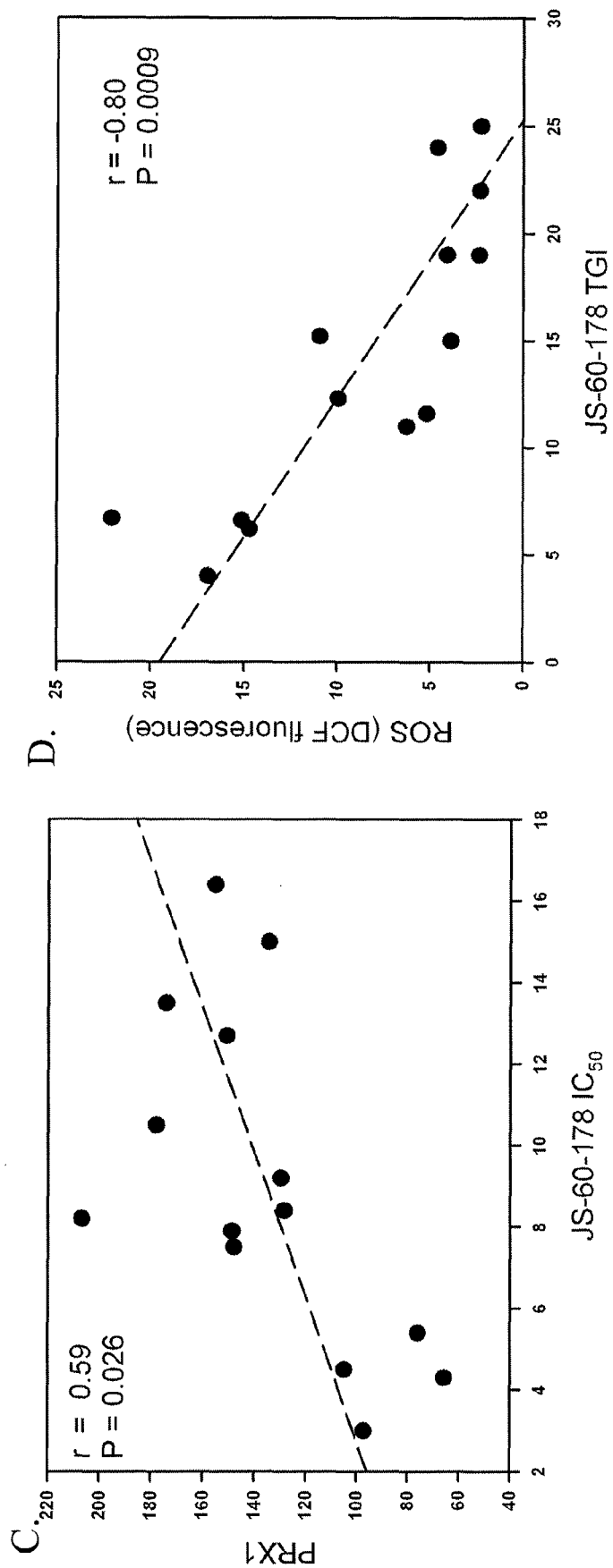
Figures 6E, 6F:
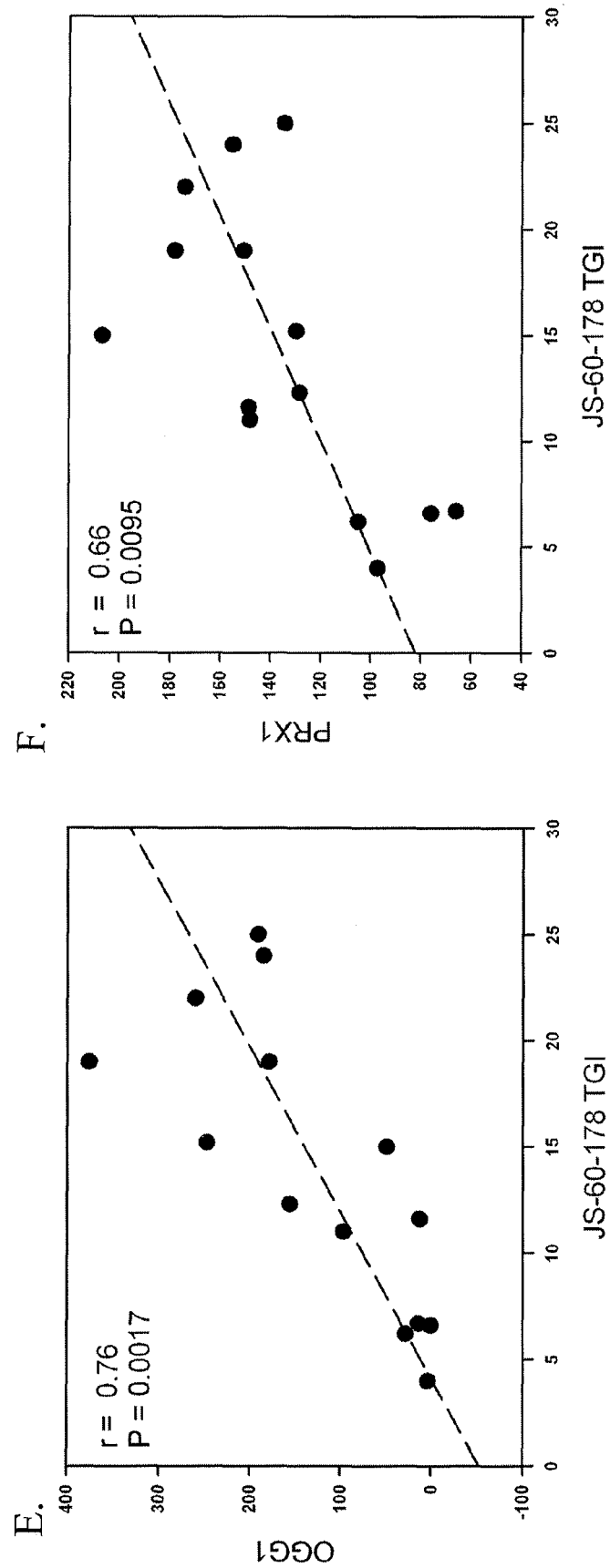

Toxicities of JS-59-183 and JS-60-178 (expressed as IC$_{50}$ and TGI concentrations) correlated with the preexisting endogenous level of ROS in NSCLC cells (FIG. 6). Other related factors, including levels of 8-oxoguanine DNA glycosylase (OGG1) and peroxide scavenging enzyme peroxiredoxin 1 (PRX1), also correlated with IC$_{50}$/TGI values for JS-59-183 and JS-60-178. As shown in Table 2, the toxicities of JS-60-178 and JS-59-183 but not olaparib correlated with endogenous levels of ROS, PRX1 and OGG1 (P≤0.05 considered significant, by Pearson linear correlation or Spearman regression analysis, when appropriate).

TABLE 2

| | | ROS | PRX1 | OGG1 |
|---|---|---|---|---|
| JS-60-178 | IC$_{50}$ | 0.002 | 0.029 | 0.006 |
| | TGI | 0.001 | 0.010 | 0.002 |
| JS-59-183 | IC$_{50}$ | 0.003 | 0.017 | 0.002 |
| | TGI | 0.002 | 0.004 | 0.001 |
| olaparib | IC$_{50}$ | NS (0.620) | NS (0.539) | NS (0.336) |
| | TGI | NS (0.530) | NS (0.546) | NS (0.350) |

The alkaline comet assay was performed as described (Romanowska et al., *Free Radical Biol. Med.*, 43: 1145-1155 (2007)). Western blot analysis was performed as described previously (Maciag et al., *J. Pharmacol. Exp. Ther.*, 336: 313-320 (2011)). Primary antibodies for cleaved caspase 7 (Cell Signaling Technology, Danvers, Mass.) were used.

Twenty-four hours treatment with JS-60-178 resulted in significant DNA strand break damage as evidenced by Comet assay. More specifically, treatment with JS-60-178 at 5 μM concentration resulted in a stronger comet signal, compared with much higher concentrations of Olaparib (20 μm). In addition, a strong apoptotic signal was observed for JS-60-178 (10 μm) and JS-59-83 (10 μm) (as evidenced by cleaved caspase 7), while the same concentration of Olaparib (10 μm) did not trigger apoptosis. DMSO alone was used as a control.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I)

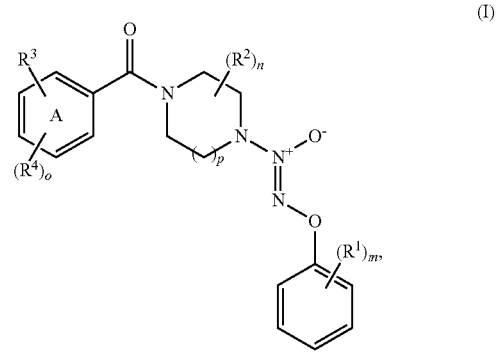

(I)

wherein
R$^1$ is selected from H, CN, NO$_2$, NCS, SCN, F, Cl, Br, I, and OCF$_3$;
R$^2$ is H;
R$^3$ is selected from

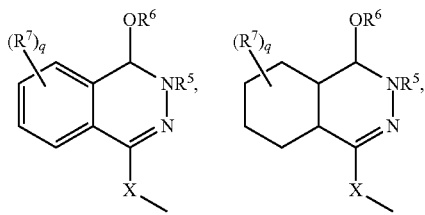

-continued

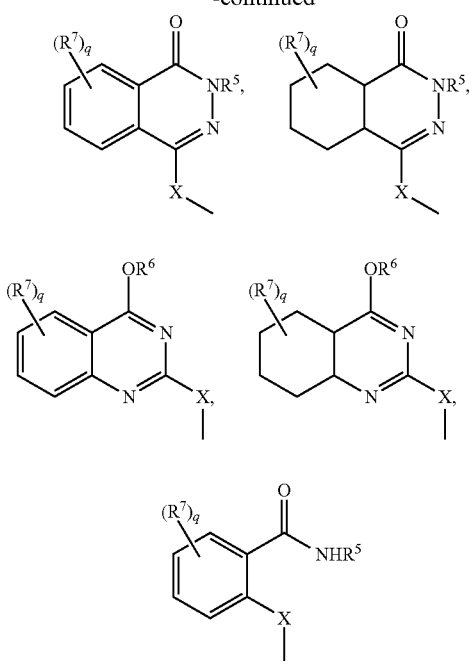

wherein
- $R^5$ and $R^6$ are each individually selected from H, acyl, and $C_{1-6}$ alkyl;
- $R^7$ is selected from H, halo, $NO_2$, cyano, OH, alkoxy, mercapto, thioalkoxy, amino, $C_{1-6}$ alkyl, $C_{1-7}$ haloalkyl, heterocycloalkyl, and aryl;
- X is selected from —$CH_2$—, —$CH_2CH_2$—, —O—, —$OCH_2$—, —$CH_2O$—, —$NR^8$—, —$CH_2NR^8$—, and —$NR^8CH_2$—; wherein $R^8$ is selected from H and $C_1$-$C_6$ alkyl; and
- q is 0 to 4;
- $R^4$ is independently selected from H, halo, OH, CN, $NO_2$, sulfonato, formyl, carboxy, mercapto, amido, amino, or a moiety selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino, and wherein each moiety is optionally further substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino;
- m is independently 0 to 5; n and o are independently 0 to 4; and
- p is 1;

or a pharmaceutically acceptable salt thereof.

2. The compound or salt of claim 1, wherein $R^4$ is H, halo, OH, or an alkyl optionally substituted with one or more substituents selected from alkyl, alkenyl, alkynyl, aryl alkyl, aryl, heterocycloalkyl, heteroaryl, heteroaryl alkyl, hydroxyalkyl, haloalkyl, aminoalkyl, alkoxy, aryloxy, thioalkoxy, acyl, acyloxy, alkoxycarbonyl, alkoxycarbonyloxy, alkylamino, and dialkylamino.

3. The compound or salt of claim 1, wherein the compound of formula (I) is selected from compounds a-d:

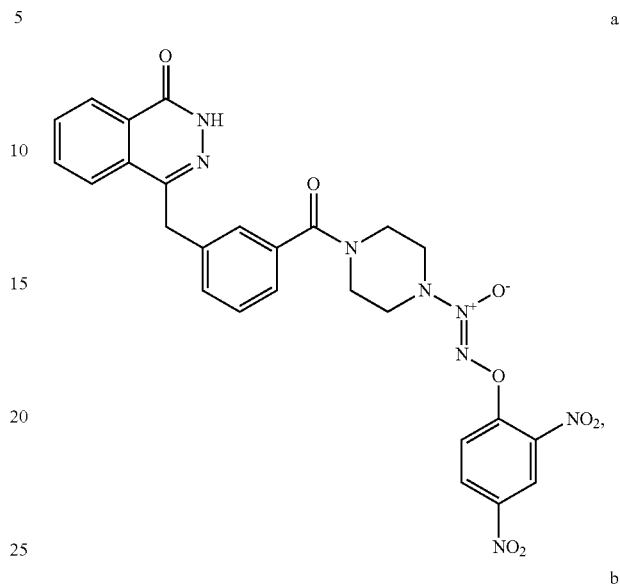

a

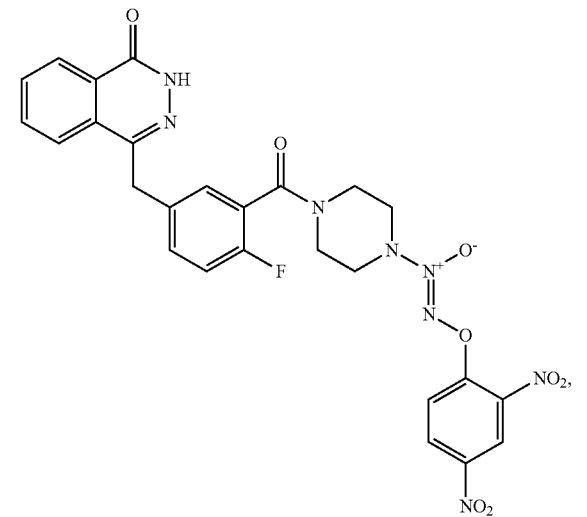

b

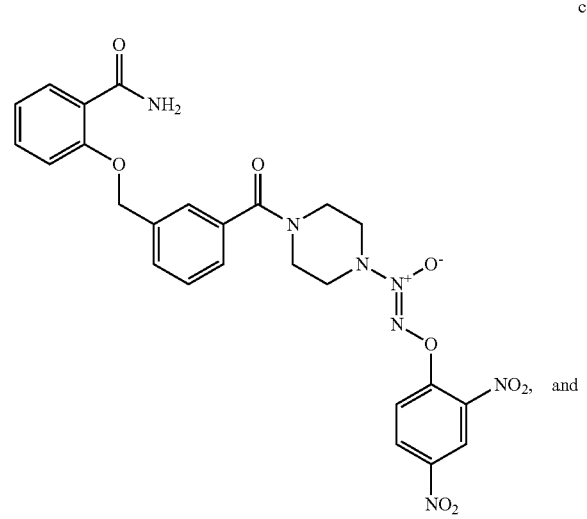

c

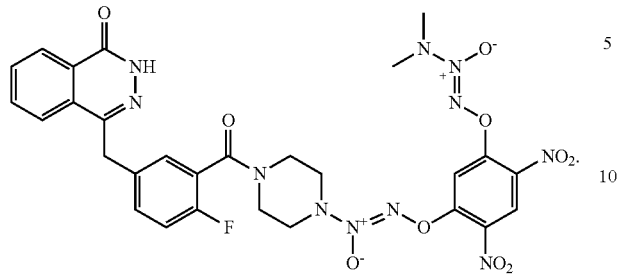

JS-65-103

4. A pharmaceutical composition comprising the compound of claim 1 or a pharmaceutically acceptable salt thereof and a pharmaceutically acceptable carrier.

5. A method of treating non-small cell lung cancer in a patient comprising administering to the patient an effective amount of the compound of claim 1 or a pharmaceutically acceptable salt thereof.

6. The method of claim 5, wherein the non-small cell lung cancer has a reactive oxygen species (ROS) content greater than the ROS content of a corresponding nonmalignant cell.

7. The method of claim 5, wherein the non-small cell lung cancer has an 8-oxo-dG DNA glycosylase (OGG1) content less than the OGG1 content of a corresponding nonmalignant cell.

8. The method of claim 5, further comprising co-administering a chemotherapeutic agent or with high energy radiation to the patient.

9. A method of enhancing chemotherapeutic treatment of a cancer patient with a chemotherapeutic agent that produces reactive oxygen species (ROS) in a cancer cell or radiation treatment of cancer, the method comprising administering to the patient an effective amount of the compound of claim 1 or a pharmaceutically acceptable salt thereof, wherein the patient has non-small cell lung cancer.

10. The compound or salt of claim 1, wherein $R^1$ is H or $NO_2$.

11. The compound or salt of claim 1, wherein $R^3$ is

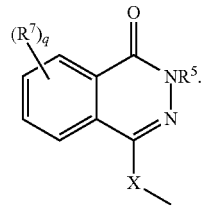

12. The compound or salt of claim 11, wherein $R^5$ is H and $C_{1-6}$ alkyl.

13. The compound or salt of claim 11, wherein q is 0.

14. The compound or salt of claim 11, wherein X is —$CH_2$— or —$CH_2CH_2$—.

15. The compound or salt of claim 1, wherein $R^3$ is

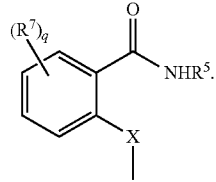

16. The compound or salt of claim 15, wherein $R^5$ is H and $C_{1-6}$ alkyl.

17. The compound or salt of claim 15, wherein q is 0.

18. The compound or salt of claim 15, wherein X is —O—, —$OCH_2$—, or —$CH_2O$—.

19. The compound or salt of claim 1, wherein $R^4$ is H or halo.

20. The compound or salt of claim 1, wherein the compound of formula (I) is compound a:

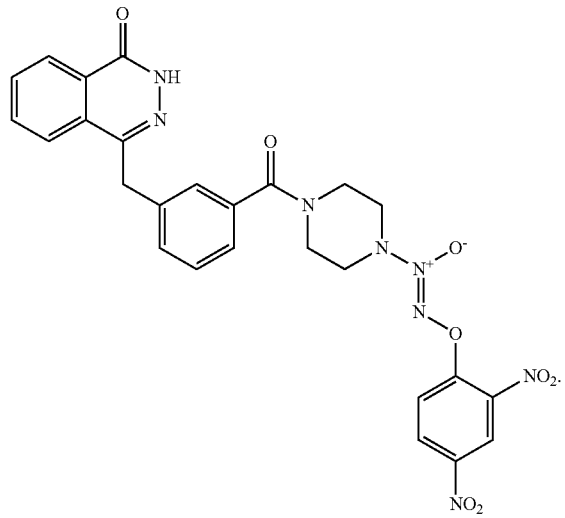

21. The compound or salt of claim 1, wherein the compound of formula (I) is compound b:

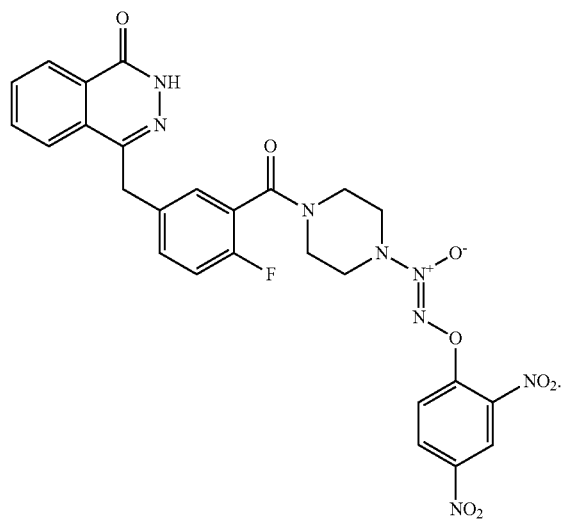

22. The compound or salt of claim 1, wherein the compound of formula (I) is compound c:
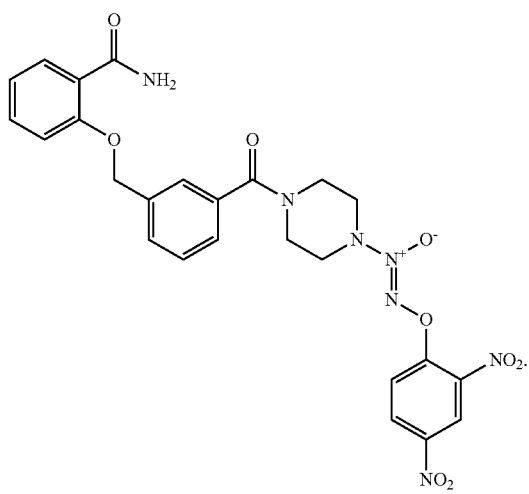
23. The compound or salt of claim 1, wherein the compound of formula (I) is compound d:
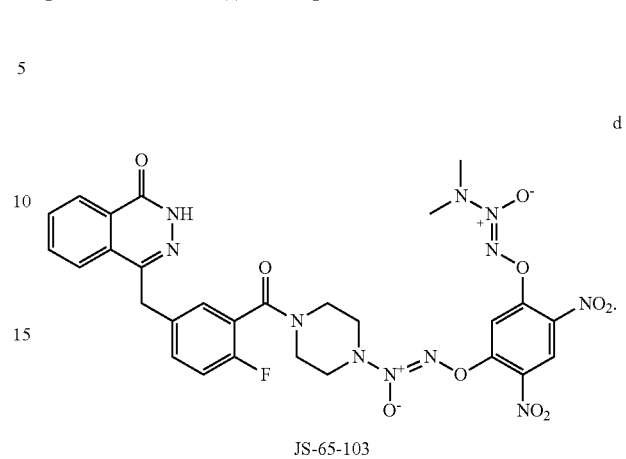
JS-65-103
* * * * *